(12) United States Patent
Northrop et al.

(10) Patent No.: US 11,535,515 B2
(45) Date of Patent: Dec. 27, 2022

(54) SULFUR RECOVERY WITHIN A GAS PROCESSING SYSTEM

(71) Applicant: ExxonMobil Upstream Research Company, Spring, TX (US)

(72) Inventors: Paul Scott Northrop, Spring, TX (US); John Timothy Cullinane, Montgomery, TX (US)

(73) Assignee: ExxonMobil Upstream Research Company, Spring, TX (US)

( * ) Notice: Subject to any disclaimer, the term of this patent is extended or adjusted under 35 U.S.C. 154(b) by 298 days.

(21) Appl. No.: 16/984,463

(22) Filed: Aug. 4, 2020

(65) Prior Publication Data
US 2021/0053827 A1 Feb. 25, 2021

Related U.S. Application Data

(60) Provisional application No. 62/889,076, filed on Aug. 20, 2019.

(51) Int. Cl.
| | | |
|---|---|---|
| *C12P 3/00* | (2006.01) |
| *C10L 3/10* | (2006.01) |
| *C01B 17/05* | (2006.01) |
| *C01B 17/04* | (2006.01) |
| *B01D 53/14* | (2006.01) |
| *B01D 53/18* | (2006.01) |
| *B01D 53/52* | (2006.01) |
| *B01D 53/78* | (2006.01) |
| *B01D 53/84* | (2006.01) |

(52) U.S. Cl.
CPC .......... *C01B 17/05* (2013.01); *B01D 53/1406* (2013.01); *B01D 53/1418* (2013.01); *B01D 53/1425* (2013.01); *B01D 53/1462* (2013.01); *B01D 53/18* (2013.01); *B01D 53/526* (2013.01); *B01D 53/78* (2013.01); *B01D 53/84* (2013.01); *C01B 17/0408* (2013.01); *C10L 3/103* (2013.01); *C12P 3/00* (2013.01); *B01D 2251/95* (2013.01); *B01D 2252/20431* (2013.01); *C10L 2290/542* (2013.01)

(58) Field of Classification Search
CPC ............... C10L 3/103; C10L 2290/542; C10L 2290/541; C01B 17/05; C01B 17/0408; C12P 3/00; B01D 53/1418; B01D 2256/245; B01D 2251/95; B01D 53/78; B01D 53/1406; B01D 53/1462; B01D 53/84; B01D 53/526; B01D 53/1425; B01D 2252/20431; B01D 53/1468; B01D 53/18
See application file for complete search history.

(56) References Cited

U.S. PATENT DOCUMENTS

| | | |
|---|---|---|
| 4,496,534 A | 1/1985 | Delaney et al. |
| 5,338,778 A | 8/1994 | Bedell et al. |
| 2015/0352463 A1 | 12/2015 | Grave et al. |
| 2016/0236140 A1 | 8/2016 | Northrop et al. |

*Primary Examiner* — Timothy C Vanoy
(74) *Attorney, Agent, or Firm* — Vorys, Sater, Seymour and Pease LLP

(57) ABSTRACT

A method for recovering sulfur within a gas processing system is described herein. The method includes contacting a natural gas stream including an acid gas with a solvent stream within a co-current contacting system to produce a sweetened natural gas stream and a rich solvent stream including an absorbed acid gas. The method also includes removing the absorbed acid gas from the rich solvent stream within a regenerator to produce a concentrated acid gas stream and a lean solvent stream. The method further includes recovering elemental sulfur from hydrogen sulfide ($H_2S$) within the concentrated acid gas stream via a sulfur recovery unit.

18 Claims, 9 Drawing Sheets

SULFUR RECOVERY WITHIN A GAS PROCESSING SYSTEM

CROSS REFERENCE TO RELATED APPLICATIONS

This application claims the priority benefit of U.S. Provisional Patent Application No. 62/889,076, filed Aug. 20, 2019, entitled SULFUR RECOVERY WITHIN A GAS PROCESSING SYSTEM.

FIELD

The present techniques provide for sulfur recovery within a gas processing system including a co-current flow scheme. More specifically, the present techniques provide for the removal of acid gas from a natural gas stream using a co-current contacting system, and the recovery of elemental sulfur from the acid gas using a sulfur recovery unit.

BACKGROUND

This section is intended to introduce various aspects of the art, which may be associated with exemplary embodiments of the present techniques. This discussion is believed to assist in providing a framework to facilitate a better understanding of particular aspects of the present techniques. Accordingly, it should be understood that this section should be read in this light, and not necessarily as admissions of prior art.

The production of hydrocarbons from a reservoir oftentimes carries with it the incidental production of non-hydrocarbon gases. Such gases include contaminants such as hydrogen sulfide ($H_2S$) and carbon dioxide ($CO_2$). When $H_2S$ and $CO_2$ are produced as part of a hydrocarbon gas stream, the raw gas stream is sometimes referred to as "sour gas." The $H_2S$ and $CO_2$ are often referred to together as "acid gases."

In addition to hydrocarbon production streams, acid gases may be associated with synthesis gas streams, or with refinery gas streams. Acid gases may also be present within so-called flash-gas streams in gas processing facilities. Further, acid gases (like $SO_2$) may be generated by the combustion of coal, natural gas, or other carbonaceous fuels.

Natural gas streams may contain not only $H_2S$ and $CO_2$, but may also contain other "acidic" impurities. These include mercaptans and other trace sulfur compounds (e.g., COS). In addition, natural gas streams may contain water. Such impurities are often removed prior to industrial or residential use. For example, natural gas streams are typically purified to concentrations of less than 4 parts per million (ppm) $H_2S$ and less than 2-3 volume percent (vol. %) $CO_2$ prior to sale. The extent to which such impurities must be removed is dictated by pipeline regulations, which help to ensure public safety and maintain the integrity of the pipeline by reducing corrosion.

Acid gas removal is an expensive and equipment-intensive process. The removal of $H_2S$ from natural gas streams is especially complicated due to the safety, health, and environmental considerations when working with $H_2S$. $H_2S$ is an extremely toxic, odorous, and corrosive gas. High levels of $H_2S$ can cause corrosion of gas production hardware if free water is present. Moreover, $H_2S$ levels above 10 ppmv (parts per million by volume) exceed the OSHA Threshold Limit Value (TLV) for safety, and levels above 100 ppmv in a breathing zone can rapidly lead to unconsciousness and death. Therefore, $H_2S$ removal is a critical function of a gas processing facility.

Furthermore, once $H_2S$ has been removed from a natural gas stream, it is often desirable to process the acid gas stream containing the $H_2S$ to recover elemental sulfur. This may be accomplished using a wide variety of sulfur recovery processes. However, conventional gas processing facilities for removing acid gases from a natural gas stream employ counter-current contactors that operate at high pressures, and some sulfur recovery processes are prone to tower plugging at high pressures.

Moreover, in some applications, the inlet gas flow rate is high, i.e., greater than approximately 2.83 million cubic meters per day (100 million standard cubic feet per day (MMSCF/D)), and the $H_2S$ concentration is relatively low, i.e., less than approximately 200 ppm. This may be the case for many shale gas applications, for example. The resulting amount of equivalent sulfur is approximately 0.76 tonnes (0.75 long tons per day (LTPD)), so $H_2S$ scavengers would be a high operating expense alternative. However, the amount of sulfur is too small to effectively employ a Claus Sulfur Recovery Unit.

One possible technique to handle this quantity of sulfur is to employ a reduction-oxidation (redox) process that uses an aqueous chelated iron solution to directly oxidize the $H_2S$ in the natural gas stream to elemental sulfur. However, because such redox processes are typically applied directly to a high-pressure natural gas stream, they are prone to tower plugging issues. Moreover, such redox processes typically require relatively large, expensive equipment that is not desirable for many applications.

SUMMARY

An exemplary embodiment provides a gas processing system. The gas processing system includes a co-current contacting system configured to contact a natural gas stream including an acid gas with a solvent stream to produce a sweetened natural gas stream and a rich solvent stream including an absorbed acid gas, and send the rich solvent stream to a regenerator. The regenerator is configured to remove the absorbed acid gas from the rich solvent stream to produce a concentrated acid gas stream and a lean solvent stream, and send the concentrated acid gas stream to a sulfur recovery unit. The sulfur recovery unit is configured to recover elemental sulfur from hydrogen sulfide ($H_2S$) within the concentrated acid gas stream.

Another exemplary embodiment provides a method for recovering sulfur within a gas processing system. The method includes contacting a natural gas stream including an acid gas with a solvent stream within a co-current contacting system to produce a sweetened natural gas stream and a rich solvent stream including an absorbed acid gas. The method also includes removing the absorbed acid gas from the rich solvent stream within a regenerator to produce a concentrated acid gas stream and a lean solvent stream. The method further includes recovering elemental sulfur from $H_2S$ within the concentrated acid gas stream via a sulfur recovery unit.

Another exemplary embodiment provides a gas processing system. The gas processing system includes a first co-current contacting system configured to contact a natural gas stream including an acid gas with a first solvent stream to produce a first partially-sweetened natural gas stream and a first rich solvent stream including a first portion of absorbed acid gas, and send the rich solvent stream to a regenerator. The gas processing system also includes a second co-current contacting system configured to contact the first partially-sweetened natural gas stream with a second solvent stream to produce a second partially-sweetened natural gas stream and a second rich solvent stream including a second portion of absorbed acid gas, and send the second rich solvent stream back into the first co-current contacting system as the first solvent stream. The gas processing system also includes a third co-current contacting system configured to contact the second partially-sweetened natural gas stream with a third solvent stream to produce a sweetened natural gas stream and a third rich solvent stream including a third portion of absorbed acid gas, and send the third rich solvent stream back into the second co-current contacting system as the second solvent stream. The regenerator is configured to remove the first portion of the absorbed acid gas from the first solvent stream to produce a concentrated acid gas stream and a lean solvent stream, send the lean solvent stream into the third co-current contacting system as the third solvent stream, and send the concentrated acid gas stream to a sulfur recovery unit. The sulfur recovery unit is configured to recover elemental sulfur from $H_2S$ within the concentrated acid gas stream.

DESCRIPTION OF THE DRAWINGS

The advantages of the present techniques are better understood by referring to the following detailed description and the attached drawings, in which.

DETAILED DESCRIPTION

Figure 1A:
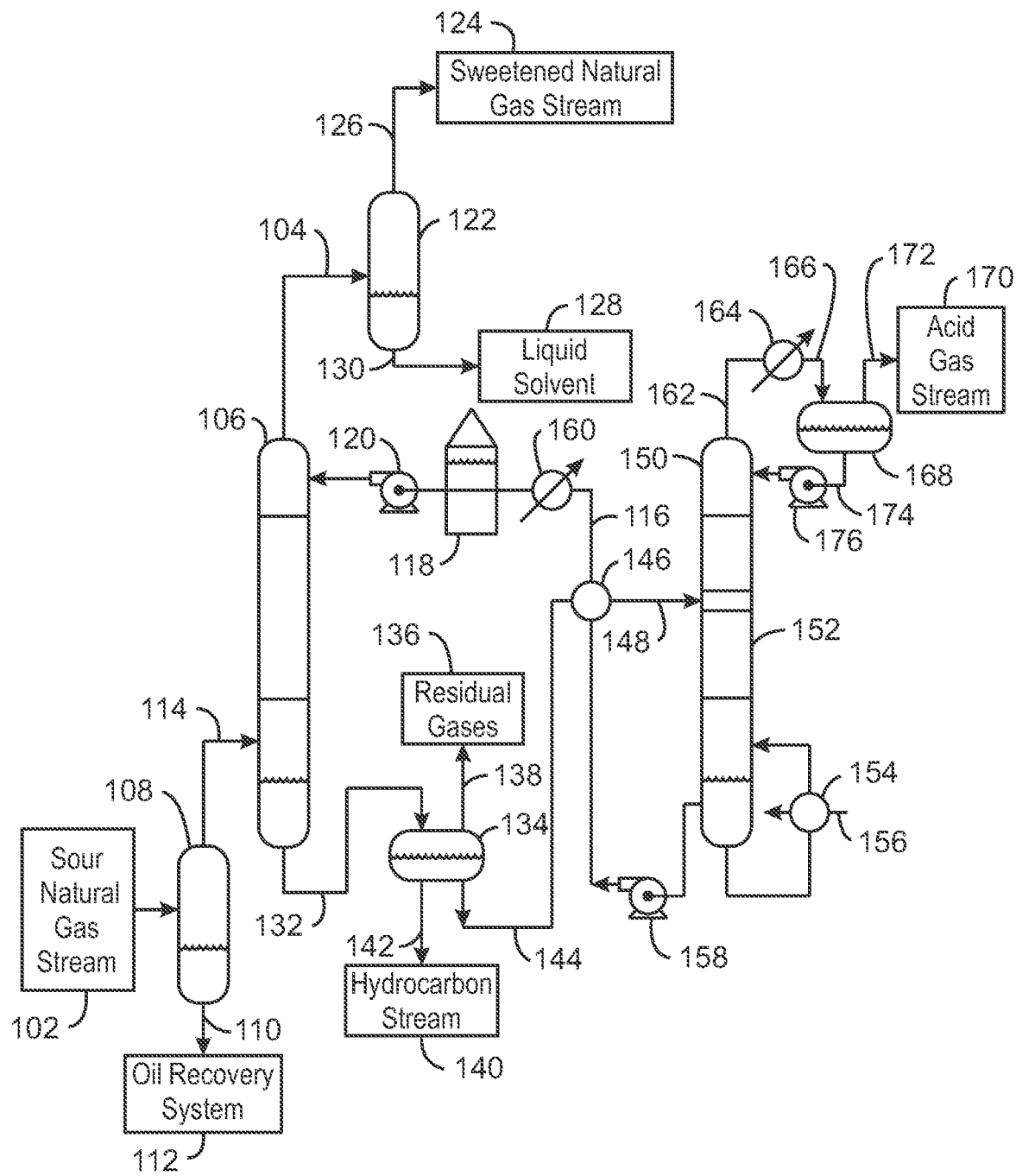
FIG. 1A is a process flow diagram of a conventional gas processing facility.

In the following detailed description section, specific embodiments of the present techniques are described. However, to the extent that the following description is specific to a particular embodiment or a particular use of the present techniques, this is intended to be for exemplary purposes only and simply provides a description of the exemplary embodiments. Accordingly, the techniques are not limited to the specific embodiments described below, but rather, include all alternatives, modifications, and equivalents falling within the true spirit and scope of the appended claims.

At the outset, for ease of reference, certain terms used in this application and their meanings as used in this context are set forth. To the extent a term used herein is not defined below, it should be given the broadest definition persons in the pertinent art have given that term as reflected in at least one printed publication or issued patent. Further, the present techniques are not limited by the usage of the terms shown below, as all equivalents, synonyms, new developments, and terms or techniques that serve the same or a similar purpose are considered to be within the scope of the present claims.

As used herein, the terms "a" and "an" mean one or more when applied to any embodiment described herein. The use of "a" and "an" does not limit the meaning to a single feature unless such a limit is specifically stated.

As used herein, the term "about" means ±10% of the subsequent number, unless otherwise stated.

"Acid gas" refers to any gas that dissolves in water, producing an acidic solution. Non-limiting examples of acid gases include hydrogen sulfide ($H_2S$), carbon dioxide ($CO_2$), sulfur dioxide ($SO_2$), carbon disulfide ($CS_2$), carbonyl sulfide (COS), mercaptans, or mixtures thereof.

The terms "approximate," "approximately," "substantial," and "substantially" mean a relative amount of a material or characteristic that is sufficient to provide the intended effect. The exact degree of deviation allowable in some cases may depend on the specific context, e.g., ±1%, ±5%, ±10%, ±15%, etc. It should be understood by those of skill in the art that these terms are intended to allow a description of certain features described and claimed without restricting the scope of these features to the precise numerical ranges provided. Accordingly, these terms should be interpreted as indicating that insubstantial or inconsequential modifications or alterations of the subject matter described are considered to be within the scope of the disclosure.

The "Claus process" is a process that is sometimes used by the natural gas and refinery industries to recover elemental sulfur from $H_2S$-containing gas streams. Briefly, the Claus process for producing elemental sulfur includes two primary sections. The first section is a thermal section wherein $H_2S$ is converted to elemental sulfur at approximately 1,800-2,200° F. (1,000-1,220° C.). No catalyst is present in the thermal section. The second section is a catalytic section wherein elemental sulfur is produced at temperatures between 400 to 650° F. (200-340° C.) over a suitable catalyst (such as alumina). The reaction to produce elemental sulfur is an equilibrium-limited reaction; hence, there are several stages in the Claus process where separations are made in an effort to enhance the overall conversion of $H_2S$ to elemental sulfur. Each stage involves heating, reacting, cooling, and separation.

"Co-current contactor" refers to a vessel that receives a stream of gas and a separate stream of solvent in such a manner that the gas stream and the solvent stream contact one another while flowing in generally the same directions within the contactor.

The term "co-currently" refers to the internal arrangement of process streams within a unit operation that can be divided into several sub-sections by which the process streams flow in the same direction.

As used herein, the term "fluid" refers to gases, liquids, and combinations of gases and liquids, as well as to combinations of gases and solids, and combinations of liquids and solids.

The term "gas" is used interchangeably with "vapor," and is defined as a substance or mixture of substances in the gaseous state as distinguished from the liquid or solid state.

Likewise, the term "liquid" means a substance or mixture of substances in the liquid state as distinguished from the gas or solid state.

A "hydrocarbon" is an organic compound that primarily includes the elements hydrogen and carbon, although nitrogen, sulfur, oxygen, metals, or any number of other elements may be present in small amounts. As used herein, the term "hydrocarbon" generally refers to components found in natural gas, oil, or chemical processing facilities. Moreover, the term "hydrocarbon" may refer to components found in raw natural gas, such as methane ($CH_4$), ethane ($C_2H_6$), $C_3$ isomers, $C_4$ isomers, benzene ($C_6H_6$), and the like.

With respect to fluid processing equipment, the term "in series" means that two or more devices are placed along a flow line such that a fluid stream undergoing fluid separation moves from one item of equipment to the next while maintaining flow in a substantially constant downstream direction. Similarly, the term "in line" means that two or more components of a fluid mixing and separating device are connected sequentially or, more preferably, are integrated into a single tubular device.

As used herein, the terms "lean" and "rich," when used with respect to the absorbent liquid removal of a selected gas component from a gas stream, are relative, merely implying, respectively, a lesser or greater degree or extent of loading or content of the selected gas component, and do not necessarily indicate or require, respectively, either that the absorbent liquid is totally devoid of the selected gas component, or that it is incapable of absorbing more of the selected gas component. In fact, it is preferred that the so-called "rich" absorbent liquid retains residual absorptive capacity. Conversely, a "lean" absorbent liquid will be understood to be capable of additional absorption, and may retain a minor concentration of gas components being removed.

The term "liquid solvent" or "solvent stream" refers to a fluid in substantially liquid phase that preferentially absorbs one component over another. For example, a liquid solvent may preferentially absorb an acid gas, thereby removing or "scrubbing" at least a portion of the acid gas component from a gas stream. Moreover, a liquid solvent may preferentially absorb one acid gas over another. The liquid solvent may be capable, at least in part, of dissolving or dispersing other substances, such as to provide or form a solution. The liquid solvent may be polar, nonpolar, neutral, protic, aprotic, or the like. The liquid solvent may include any suitable element, molecule, or compound, such as methanol, ethanol, propanol, glycols, ethers, ketones, other alcohols, amines, salt solutions, or the like. The liquid solvent may include physical solvents, chemical solvents, or the like. The liquid solvent may operate by any suitable mechanism, such as physical absorption, chemical absorption, chemisorption, physisorption, adsorption, pressure swing adsorption, temperature swing adsorption, or the like. Specific liquid solvents that are useful for acid gas absorption include, but are not limited to, monoethanolamine (MEA), 2(2-aminoethoxy) ethanol [Diglycolamine® (DGA)], diethanolamine (DEA), diisopropanolamine (DIPA), methyldiethanolamine (MDEA), triethyleneamine, FLEXSORB® SE, 2-amino-2-methyl-1-propanol (AMP), or formulated amines such as FLEXSORB® SE PLUS, the UCARSOL™ family of products, or formulated MDEA solutions.

"Natural gas" refers to a multi-component gas obtained from a crude oil well or from a subterranean gas-bearing formation. The composition and pressure of natural gas can vary significantly. A typical natural gas stream contains methane ($CH_4$) as a major component, i.e., greater than 50 mole percent (mol. %) of the natural gas stream. The natural gas stream can also contain ethane ($C_2H_6$), higher molecular weight hydrocarbons (e.g., $C_3$-$C_{20}$ hydrocarbons), acid gases (e.g., carbon dioxide and hydrogen sulfide), or any combinations thereof. The natural gas can also contain minor amounts of contaminants such as water, nitrogen, iron sulfide, wax, crude oil, or any combinations thereof. The natural gas stream may be substantially purified prior to use in embodiments described herein, so as to remove compounds that may act as poisons.

"Non-absorbing gas" means a gas that is not significantly absorbed by a solvent during a gas treating or conditioning process.

As used herein, "purification" includes separation processes by which impurities that may cause problems to downstream processes are removed.

The term "sour natural gas stream" refers to a natural gas stream that contains undesirable quantities of acid gas components.

The term "sweetened natural gas stream" refers to a natural gas stream that has had at least a portion of acid gas components removed.

Overview

The present techniques provide for sulfur recovery within a gas processing system including a co-current flow scheme. The co-current flow scheme utilizes any number of co-current contacting systems connected in series (or any other suitable configuration) within a pipe. A natural gas stream and a liquid solvent stream move together, i.e., co-currently, within the co-current contacting systems. In some embodiments, the natural gas stream and the solvent stream move together generally along the longitudinal axis of the co-current contacting system.

Each co-current contacting system within the gas processing system includes a co-current contactor that facilitates the absorption of acid gases, including hydrogen sulfide ($H_2S$) and carbon dioxide ($CO_2$), into the solvent stream. In addition, each co-current contacting system includes a separator that is capable of separating the natural gas stream from the solvent stream with the absorbed acid gas, producing a sweetened natural gas stream.

The solvent stream is then sent to a regenerator. The regenerator removes the absorbed acid gas from the solvent stream, producing a lean solvent stream that may be reused within the co-current contacting systems and a concentrated acid gas stream including $H_2S$ and $CO_2$. According to embodiments described herein, the acid gas stream is then sent to a sulfur recovery unit. The sulfur recovery unit produces elemental sulfur from the $H_2S$ within the acid gas stream.

Conventional Gas Processing Facility

FIG. 1A is a process flow diagram of a conventional gas processing facility 100. The gas processing facility 100 is used to remove acid gases, such as $H_2S$ and $CO_2$, from a sour natural gas stream 102, generating a sweetened natural gas stream 104. This is accomplished by flowing the sour natural gas stream 102 into a contactor 106, which removes the acid gases from the sour natural gas stream 102. The sweetened natural gas stream 104 is then flowed out of the contactor 106 as an overhead stream. In addition, residual water and acid gas components are removed in connection with a subsequent process, as discussed further herein.

The sour natural gas stream 102 may be a raw natural gas stream obtained from a subsurface reservoir via any suitable type of hydrocarbon recovery operation. The sour natural gas stream 102 may include a non-absorbing gas, such as methane. The sour natural gas stream 102 may also include about 0.01% to about 10% $H_2S$ and about 1% to about 10% $CO_2$, along with the hydrocarbon gas. In addition, the sour natural gas stream 102 may include other impurities, such as water.

As shown in FIG. 1A, the sour natural gas stream 102 is flowed into an inlet separator 108 upon entry into the gas processing facility 100. When entering the inlet separator 108, the sour natural gas stream 102 may be under a large amount of pressure. However, the pressure of the sour natural gas stream 102 may vary considerably, depending on the characteristics of the subsurface reservoir from which the gas product is produced. For example, the pressure of the sour natural gas stream 102 may range between atmospheric pressure and several thousand psig. For natural gas treating applications, the pressure of the sour natural gas stream 102 may be boosted to about 689 kPa (100 psig), or about 3.45 MPa (500 psig), or greater, if desired.

The inlet separator 108 cleans the sour natural gas stream 102, for example, to prevent foaming of liquid solvent during the acid gas treatment process. This is accomplished by separating the sour natural gas stream 102 into liquid-phase components and gas-phase components. The liquid-phase components include heavy hydrocarbons, water, and impurities such as brine and drilling fluids. Such components are flowed out of the inlet separator 108 via a bottoms line 110, and are sent to an oil recovery system 112. The gas-phase components include natural gas and some amount of impurities, such as acid gases and water. Such components are flowed out of the inlet separator 108 as the overhead natural gas stream 114.

From the inlet separator 108, the overhead natural gas stream 114 is flowed into the contactor 106. The contactor 106 uses a lean solvent stream 116 to absorb acid gases in the natural gas stream 114. The lean solvent stream 116 may be a chemical solvent, such as a primary amine, a secondary amine, or a tertiary amine. More specifically, the lean solvent stream 116 may be any solvent that is useful for acid gas absorption.

The lean solvent stream 116 is stored in a solvent tank 118. A pump 120 forces the lean solvent stream 116 from the solvent tank 118 into the contactor 106 under suitable pressure. For example, the pump 120 may boost the pressure of the lean solvent stream 116 to about 1,000 psig or higher, depending on the pressure of the sour natural gas stream 102.

Once inside the contactor 106, gas within the natural gas stream 114 moves upward through the contactor 106. Typically, trays (or packing or other internal structures) are provided within the contactor 106 to create indirect flow paths for the natural gas stream 114 and to create interfacial area between the gas and liquid phases. At the same time, the liquid from the lean solvent stream 116 moves downward and across the succession of trays in the contactor 106. The trays aid in the interaction of the natural gas stream 114 with the lean solvent stream 116.

The contactor 106 operates on the basis of a counter-current flow scheme. In other words, the natural gas stream 114 is directed through the contactor 106 in one direction, while the lean solvent stream 116 is directed through the contactor 106 in the opposite direction. As the two fluid materials interact, the down-flowing lean solvent stream 116 absorbs acid gases from the up-flowing natural gas stream 114 to produce the sweetened natural gas stream 104.

Upon exiting the contactor 106, the sweetened natural gas stream 104 is flowed through an outlet separator 122. The outlet separator 122, also referred to as a scrubber, allows any liquid solvent carried over from the contactor 106 to fall out of the sweetened natural gas stream 104. The outlet separator 122 may also be used as a water wash vessel to capture vapor-phase solvent. A final sweetened natural gas stream 124 is flowed out of the outlet separator 122 via an overhead line 126. Any residual liquid solvent 128 drops out through a bottoms line 130.

A rich solvent stream 132 flows from the bottom of the contactor 106. The rich solvent stream 132 is a solvent solution that includes absorbed acid gases. The rich solvent stream 132 may be at a relatively high temperature, such as about 32.2° C. (90° F.) to about 38.9° C. (102° F.), or higher. In various embodiments, the gas processing facility 100 includes equipment for regenerating the lean solvent stream 116 from the rich solvent stream 132, as discussed further herein.

From the contactor 106, the rich solvent stream 132 is flowed into a flash drum 134. The flash drum 134 may operate at a pressure of about 345 kPA (50 psig) to 1,034 kPa (150 psig), for example. Residual gases 136, such as acid gases and methane, are flashed out of the flash drum 134 via an overhead line 138. The residual gases 136 captured in the overhead line 138 may be reduced to an acid gas content of about 100 ppm if contacted with a small amount of fresh amine-based solvent. This concentration of acid gases is small enough that the residual gases 136 can be used as fuel gas for the gas processing facility 100.

In addition, any entrained heavier hydrocarbons, such as hexane or benzene, within the rich solvent stream 132 are captured via skimming within the flash drum 134. The resulting skimmed hydrocarbon stream 140 is flowed out of the flash drum 134 via a bottoms line 142.

Further, as the temperature and pressure of the rich solvent stream 132 drops within the flash drum 134, the hydrocarbons within the rich solvent stream 132 are separated out, producing a partially-purified solvent stream 144. The partially-purified solvent stream 144 is then released from the flash drum 134. The partially-purified solvent stream 144 is flowed through a heat exchanger 146. Within the heat exchanger 146, the partially-purified solvent stream 144 is heated via heat exchange with the lean solvent stream 116.

The resulting high-temperature solvent stream 148 is directed into a regenerator 150. The regenerator 150 is a large-diameter vessel that operates at a pressure of about 103 to 165 kPa (15 to 25 psig). The regenerator 150 includes a stripper portion 152, which typically includes trays or other internals, and a reboiler 154. A heat source 156 is provided to the reboiler 154 to generate vapor traffic within the regenerator 150. The reboiler 154 typically uses stream as its heat source to boil off water, $H_2S$, and $CO_2$ from the high-temperature solvent stream 148.

The regenerator 150 produces the lean solvent stream 116, which is recycled for reuse in the contactor 106. Specifically, the lean solvent stream 116 exits the regenerator 150 and passes through a lean solvent booster pump 158, which increases the pressure of the lean solvent stream 116. The lean solvent stream 116 then passes through the heat exchanger 146 and a cooler 160. The cooler 160 chills the lean solvent stream 116 down to 37.8° C. to 51.7° C. (100° F. to 125° F.), for example, and ensures that the lean solvent stream 116 is not flashing before being returned to the solvent tank 118. In some cases, the solvent tank 118 may be stored outside the circuit, in which case the lean solvent stream 116 will bypass the solvent tank 118 and pass directly to the pump 120.

Stripped overhead gas from the regenerator 150 containing concentrated $H_2S$ and $CO_2$ exits the regenerator 150 as an impurities stream 162. The impurities stream 162 is flowed into a condenser 164, which cools the impurities stream 162. The condenser 164 may be an air fan cooler or a heat exchanger using seawater, for example. Cooling the impurities stream 162 serves to knock out water, which helps to minimize the required water make-up. Given the presence of acid gases and free water, this portion of the gas processing facility 100 is typically clad with high-alloy metal.

The cooled impurities stream 166 then flows into a reflux accumulator 168. The reflux accumulator 168 separates any remaining liquid from the cooled impurities stream 166, producing a substantially-purified acid gas stream 170 that is flowed out of the reflux accumulator 168 via an overhead line 172. The $H_2S$ within the acid gas stream 170 may then be converted to elemental sulfur using a sulfur recovery unit (not shown), and the $CO_2$ within the acid gas stream 170 may be sequestered via compression. In addition, a wet residual solvent stream 174 may be flowed out of the bottom of the reflux accumulator 168. The wet residual solvent stream 174 may be flowed through a pump 176, which may boost the pressure of the wet residual solvent stream 174 before it is reintroduced to the regenerator 150.

The process flow diagram of FIG. 1A is not intended to indicate that the gas processing facility 100 is to include all of the components shown in FIG. 1A. Further, any number of additional components may be included within the gas processing facility 100, depending on the details of the specific implementation. For example, the gas processing facility 100 may include any suitable types of heaters, chillers, condensers, liquid pumps, gas compressors, blowers, bypass lines, other types of separation and/or fractionation equipment, valves, switches, controllers, pressure-measuring devices, temperature-measuring devices, level-measuring devices, or flow-measuring devices, among others.

In some embodiments, a solvent that preferentially removes $H_2S$ molecules over $CO_2$ molecules is used within the gas processing facility 100. For example, tertiary amines typically do not effectively strip out $CO_2$ as quickly as $H_2S$. Therefore, such solvents are useful for removing $H_2S$ from shale gas, which often includes above-specification concentrations of $H_2S$ but acceptable levels of $CO_2$. Moreover, two separate gas processing facilities 100 may be sequentially operated, with one configured to strip out primarily $H_2S$, and the other configured to strip out primarily $CO_2$. A separate $CO_2$ stream that is substantially free of $H_2S$ may also be generated.

Regardless of the application and the solvent used, the disadvantage of gas processing systems that include counter-current flow schemes, such as the conventional gas processing facility 100 of FIG. 1A, is that comparatively low velocities are required to avoid entrainment of the down-flowing liquid solvent in the sour natural gas stream 102. Also, relatively long distances are required for disengagement of the liquid droplets from the sour natural gas stream 102. Depending on the flow rate of the sour natural gas stream 102, the contactor 106 can be greater than 4.6 meters (15 feet) in diameter and more than 30.5 meters (100 feet) tall. For high-pressure applications, the vessel has thick, metal walls. Consequently, counter-current contactor vessels can be large and very heavy. This is expensive and undesirable, particularly for offshore oil and gas recovery applications.

In the gas processing facility 100 of FIG. 1A, the contactor 106 includes a single contacting tower. However, in some applications, more than one contacting tower may be used. In addition, very large contactors may be used for high-volume, high-pressure applications. In the case of low-pressure applications, such as $CO_2$ removal from flue gas at a power generation plant, it is estimated that a 15.2 meter by 15.2 meter (50 foot by 50 foot) duct contactor would be used for a relatively small, 500 megawatt power plant flue gas application. Many hundreds of liters (gallons) per minute of solvent would also be flowed through the contactor. Thus, such operations may become very costly.

Further, the internals of the contactor 106 can make it susceptible to wave motion in an offshore environment. Therefore, it may be desirable to have a mass transfer process that does not rely on conventional tower internals. For example, it may be desirable to utilize a series of low pressure-drop, small contacting devices to remove $CO_2$ or $H_2S$ from flash-gas streams.

Embodiments described herein utilize a co-current flow scheme as an alternative to the counter-current flow scheme demonstrated in the contactor 106 of FIG. 1A. The co-current flow scheme utilizes co-current contacting systems connected in series within a pipe. A natural gas stream and a liquid solvent move together, i.e., co-currently, within the co-current contacting systems. In some embodiments, the natural gas stream and the liquid solvent move together generally along the longitudinal axis of the respective co-current contacting system. In general, co-current contactors are not subject to the same hydraulic capacity limitations as counter-current contactors. As a result, co-current contactors tend to be smaller than counter-current contactors that utilize standard packed or trayed towers. Furthermore, the longer contacting time in a standard counter-current contactor limits the effectiveness of a selective solvent, while the short contact time of the disclosed co-current contactors permits carbon dioxide to slip through significantly improves solvent selectivity, thereby enabling a reduction in size needed for the contacting equipment.

Applying the LO-CAT® DirectTreat Process Directly to a Natural Gas Stream

Figure 1B:
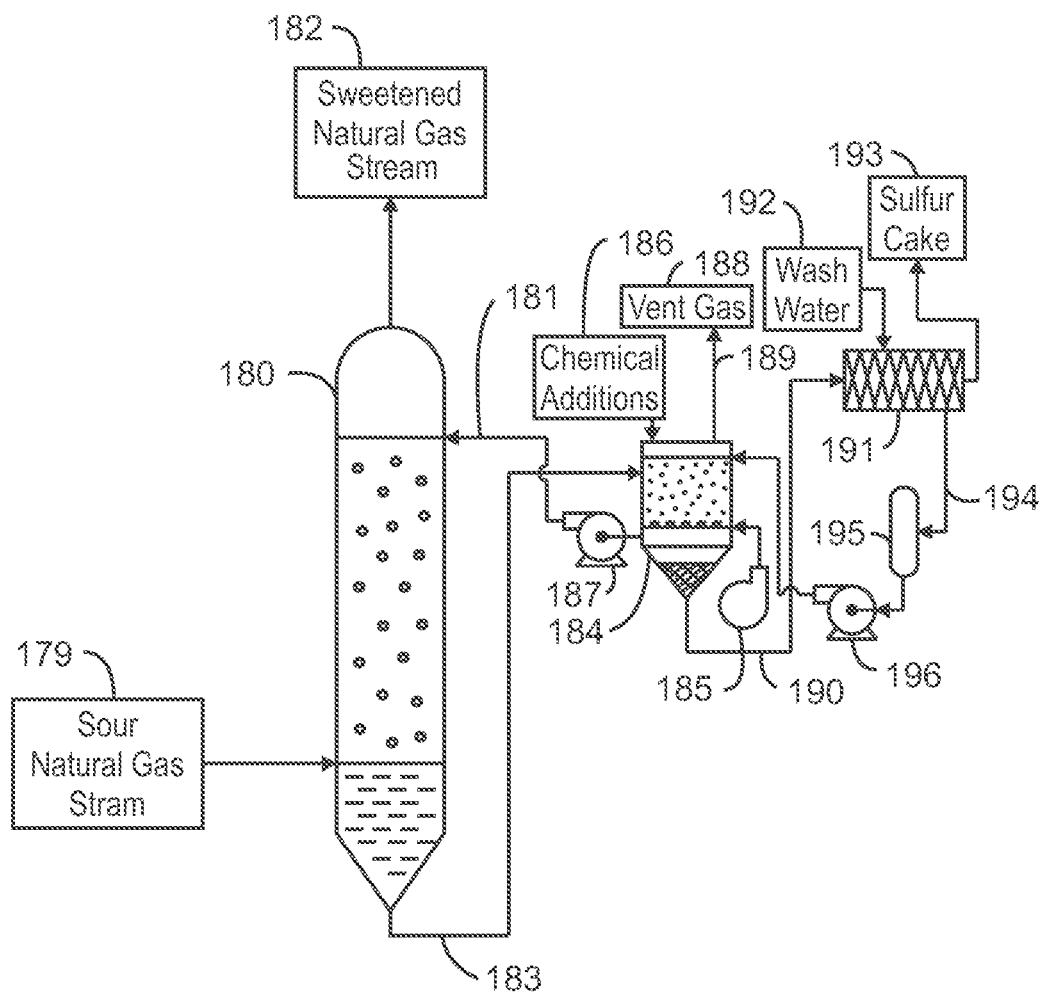
FIG. 1B is a process flow diagram of a sulfur recovery unit that employs the LO-CAT® DirectTreat process to directly treat a sour natural gas stream.

FIG. 1B is a process flow diagram of a sulfur recovery unit 178 that employs the LO-CAT® DirectTreat process to directly treat a sour natural gas stream 179. The sour natural gas stream 179 may be a raw natural gas stream obtained from a subsurface reservoir via any suitable type of hydrocarbon recovery operation. The sour natural gas stream 179 may include a non-absorbing gas, such as methane. The sour natural gas stream 179 may also include about 0.01% to about 10% $H_2S$ and about 1% to about 10% $CO_2$, along with the hydrocarbon gas. In addition, the sour natural gas stream 179 may include other impurities, such as water.

The LO-CAT® technology was developed by Merichem Company to provide an efficient method for carrying out the modified Claus reaction. The LO-CAT® process involves using a liquid reduction-oxidation (redox) catalyst to convert $H_2S$ to solid elemental sulfur by carrying out the direct oxidation of $H_2S$, as shown in Eq. 1.

$$H_2S + \tfrac{1}{2}O_2 \rightarrow H_2O + S° \text{ (Direct } H_2S \text{ Oxidation)} \quad \text{(Eq. 1)}$$

The direct oxidation reaction is divided into five steps, as shown in Eq. 2-6.

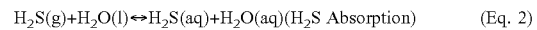
$$H_2S(g) + H_2O(l) \leftrightarrow H_2S(aq) + H_2O(aq)(H_2S \text{ Absorption}) \quad \text{(Eq. 2)}$$

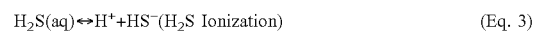
$$H_2S(aq) \leftrightarrow H^+ + HS^- (H_2S \text{ Ionization}) \quad \text{(Eq. 3)}$$

$$HS^- + 2Fe^{+3} \leftrightarrow S° + 2Fe^{+2} + H^+ (\text{Sulfide Oxidation}) \quad \text{(Eq. 4)}$$

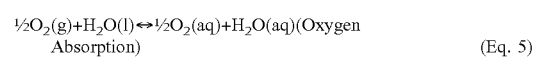
$$\tfrac{1}{2}O_2(g) + H_2O(l) \leftrightarrow \tfrac{1}{2}O_2(aq) + H_2O(aq)(\text{Oxygen Absorption}) \quad \text{(Eq. 5)}$$

$$\tfrac{1}{2}O_2(aq)+H_2O+2Fe^{+2}\rightarrow 2OH^-+2Fe^{+3} \text{(Iron Oxidation)} \quad \text{(Eq. 6)}$$

Eq. 2 and 3 represent the absorption of $H_2S$ into the aqueous, chelated iron solution and its subsequent ionization, while Eq. 4 represents the oxidation of hydrosulfide ions to elemental sulfur and the reduction of the ferric (active) iron to the ferrous (inactive) state. Eq. 5 and 6 represent the absorption of oxygen (from ambient air) into the aqueous solution, followed by oxidation of the ferrous iron back to the ferric state.

Eq. 4 and 6 are very rapid. Consequently, LO-CAT systems generally produce relatively small amounts of byproduct thiosulfate ions. However, Eq. 2 and 5 are relatively slow and are the rate controlling steps in a LO-CAT System. In the overall chemical reaction, the iron serves as an electron donor and acceptor, i.e., a reagent, and as a catalyst in accelerating the reaction. The chelating agents do not take part in the process chemistry. Their role is simply to hold the iron ions in solution. Neither ferrous ($Fe^{+2}$) nor ferric ($Fe^{+3}$) ions are very soluble or very stable in aqueous solutions. Therefore, the chelating agents wrap around the iron ions, preventing the iron ions from forming precipitates.

Figure 3A:
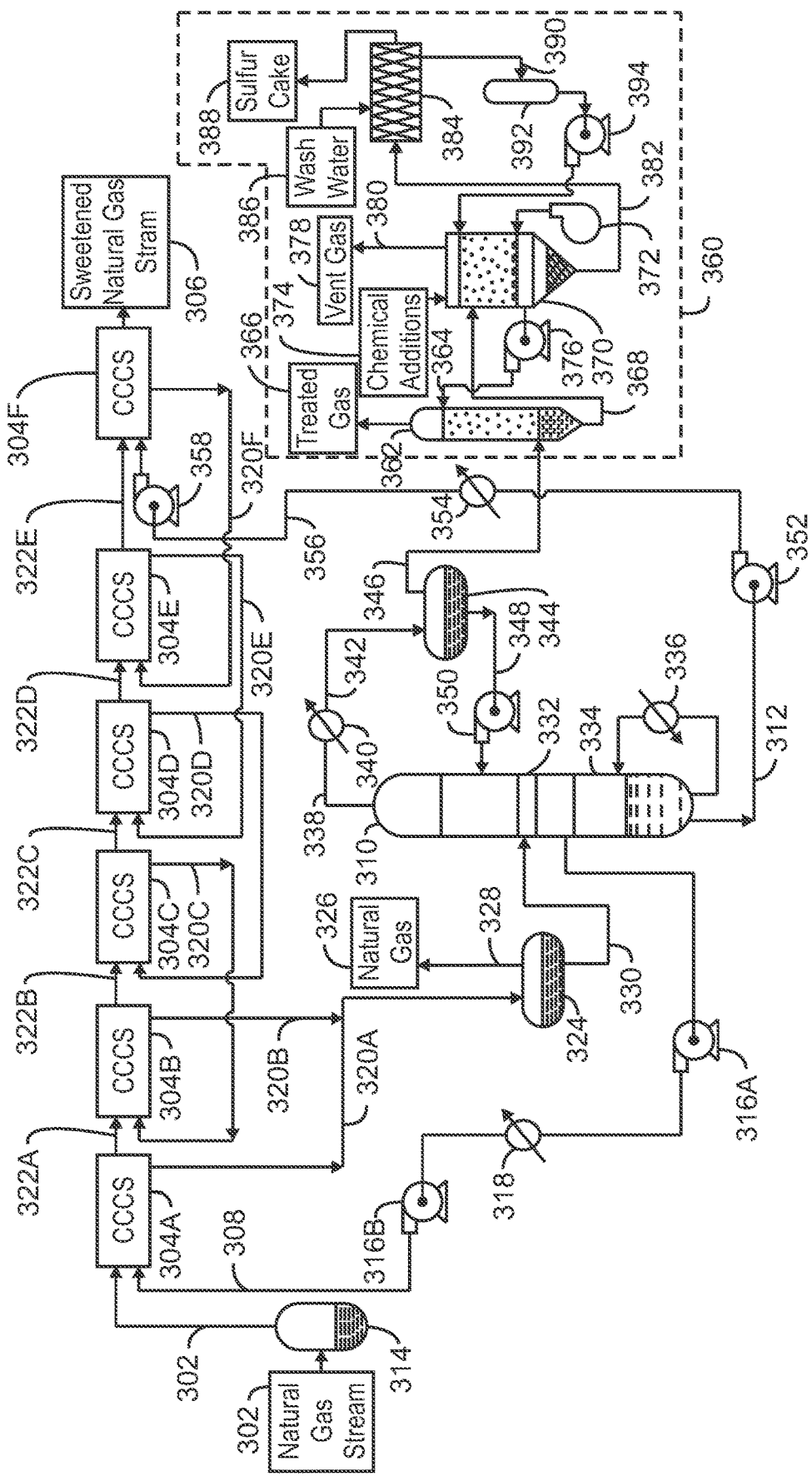
FIG. 3A is a process flow diagram of another gas processing system that includes a co-current flow scheme and is configured for sulfur recovery using the LO-CAT® DirectTreat process.
Figure 3B:
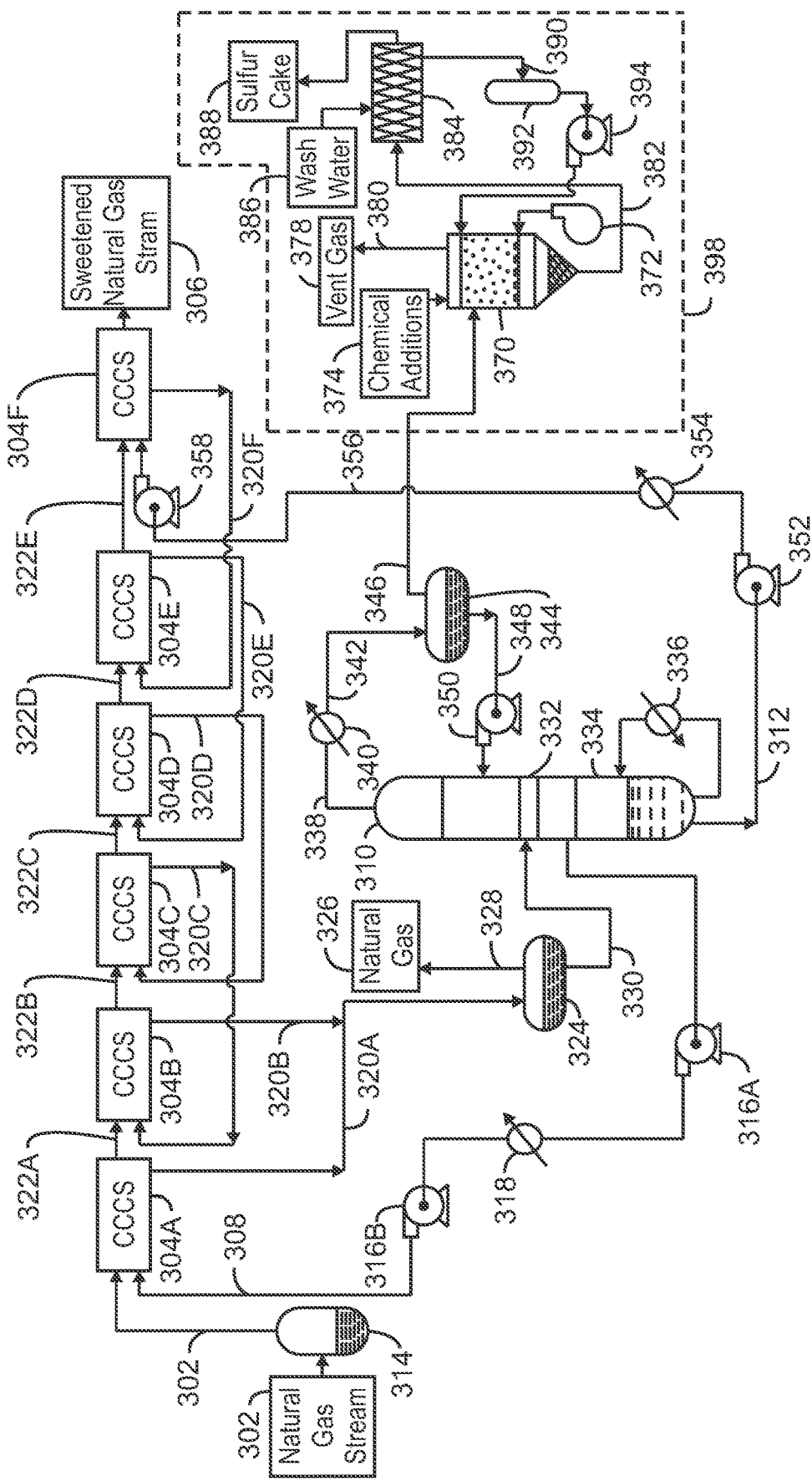
FIG. 3B is a process flow diagram of another gas processing system that includes a co-current flow scheme and is configured for sulfur recovery using the LO-CAT® AutoCirc process.

The LO-CAT® technology can generally divided into two different processes, the LO-CAT® DirectTreat process, which is described with respect to FIGS. 1B and 3A, and the LO-CAT® AutoCirc process, which described with respect to FIG. 3B. As shown in FIG. 1B, the sour natural gas stream 179 is flowed into an absorber 180 within the sulfur recovery unit 178. Within the absorber 180, the $H_2S$ within the sour natural gas stream 179 reacts with a chelated iron solution 181 according to Eq. 2-4, producing sulfur. The process produces a sweetened natural gas stream 182 and a concentrated solution 183 including the chelated iron solution 181 and sulfur.

The sweetened natural gas stream 182 is flowed out of the top of the absorber 180, while the concentrated solution 183 is flowed out of the bottom of the absorber 180 and into an oxidizer 184. Within the oxidizer 184, air from an air blower 185 moves uniformly through the concentrated solution 183. This results in the reduction of iron back to an active state according to Eq. 5 and 6, thus regenerating the chelated iron solution 181. In addition, chemical additions 186 are added to the chelated iron solution 181 within the oxidizer 184 to replace trace quantities of the chelated iron solution 181 that are naturally lost through displacement, chelate degradation, and byproduct salt formation. The regenerated chelated iron solution 181 including the chemical additions 186 is then pumped back into the absorber 180 via a pump 187.

Vent gas 188 is flowed out of the top of the oxidizer 184 via an overhead line 189. The vent gas 188 may include residual nitrogen ($N_2$), oxygen ($O_2$), water ($H_2O$), carbon dioxide ($CO_2$), and trace hydrocarbons that were removed from the concentrated solution 183 within the oxidizer 184.

The sulfur within the concentrated solution 183 settles in the conical bottom section of the oxidizer 184, producing a sulfur slurry 190 that is then pumped into a sulfur filter 191. Within the sulfur filter 191, the sulfur slurry 190 is contacted with wash water 192, producing a sulfur cake 193 and a filtrate 194 including residual chelated iron solution. The filtrate 194 is then sent to a filtrate tank 195. From the filtrate tank 195, the filtrate 194 is pumped back into the oxidizer 184 via a pump 196.

According to the embodiment shown in FIG. 1B, the LO-CAT® process is used for the direct treatment of a sour natural gas stream at high pressure. However, in such high-pressure applications, the LO-CAT® process is prone to sulfur plugging issues. Therefore, embodiments described herein provide for the application of the LO-CAT® process (or another suitable sulfur recovery process) to an acid gas stream that has been removed from a sour natural gas stream using one or more upstream co-current contacting systems, as described further with respect to FIGS. 2, 3A, 3B, and 4. The use of one or more co-current contacting systems may allow the sulfur recovery unit to be operated at a lower pressure, thus resulting in fewer sulfur plugging issues. Furthermore, according to embodiments described herein, using the LO-CAT® process in conjunction with one or more co-current contacting systems (which is highly effective in separating sulfur compounds from the gas stream) reduces the need for significant subsequent sulfur recovery operations, and thereby allows the LO-CAT® sulfur recovery equipment to be much more compact than the sulfur recovery equipment that is typically used in conjunction with a conventional counter-current contactor, such as the contactor 106 described with respect to FIG. 1A.

Gas Processing Systems with Co-Current Flow Schemes and Sulfur Recovery Units

Figure 2:
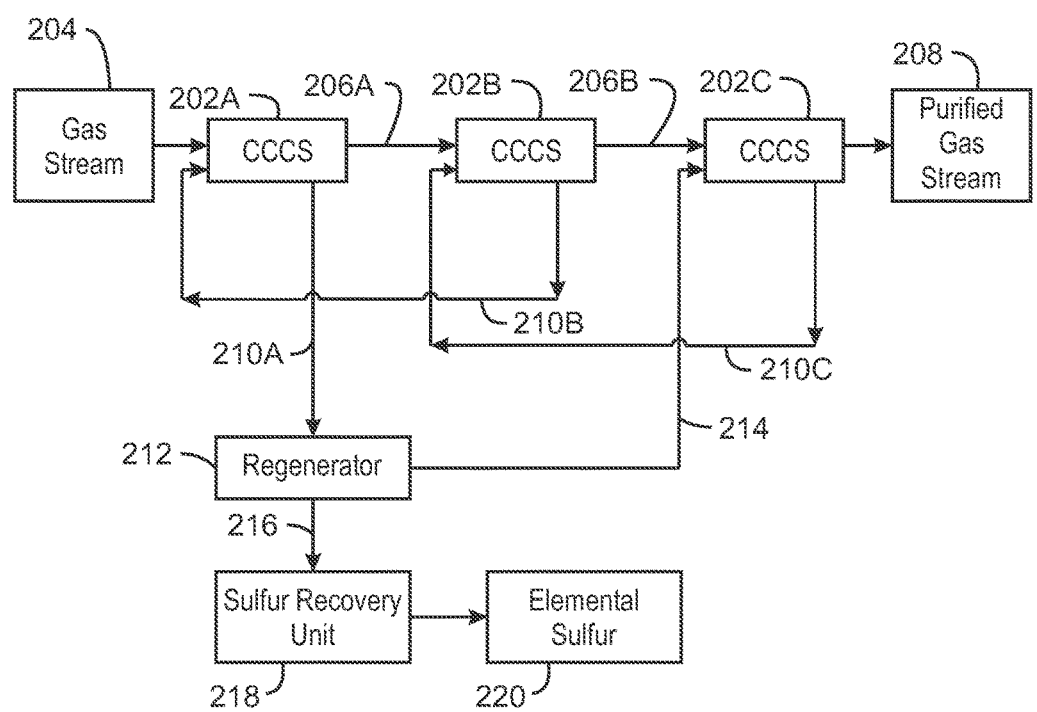
FIG. 2 is a simplified process flow diagram of a gas processing system that includes a co-current flow scheme and is configured for sulfur recovery.

FIG. 2 is a simplified process flow diagram of a gas processing system 200 that includes a co-current flow scheme and is configured for sulfur recovery. The gas processing system 200 includes a number of co-current contacting systems 202A-C. Specifically, the gas process system 200 includes a first co-current contacting system 202A, a second co-current contacting system 202B, and a third co-current contacting system 202C. Each co-current contacting system 202A-C includes a co-current contactor and a separation system, as described further with respect to FIGS. 5, 6A, and 6B. The co-current contacting systems 202A-C are configured to purify a gas stream 204 by removing impurities, such as $H_2S$ and $CO_2$, from the gas stream 204.

According to the embodiment shown in FIG. 2, the gas stream 204 is flowed into the first co-current contacting system 202A. The first co-current contacting system 202A generates a first partially purified gas stream 206A, which is flowed from the first co-current contacting system 202A to the second co-current contacting system 202B. The second co-current contacting system 202B then generates a second partially purified gas stream 206B, which is flowed from the second co-current contacting system 202B to the third co-current contacting system 202C. The third co-current contacting system 202C generates a final purified gas stream 208.

Each of the first, second, and third co-current contacting systems 202A-C also generates respective rich solvent streams 210A, 210B, and 210C. The third rich solvent stream 210C is directed back to the second co-current contacting system 202B, and the second rich solvent stream 210B is directed back to the first co-current contacting system 202A.

The first rich solvent stream 210A is sent to a regenerator 212. The regenerator 212 removes the impurities from the first rich solvent stream 210A, producing a lean solvent stream 214 and an acid gas stream 216. The lean solvent stream 214 is directed into the third co-current contacting system 202C, and the acid gas stream 216 is sent to a sulfur recovery unit 218.

The sulfur recovery unit 218 generates elemental sulfur 220 from the $H_2S$ within the acid gas stream 216. According to embodiments described herein, the sulfur recovery unit 218 may utilize any suitable process for sulfur recovery, as described further with respect to FIGS. 3A, 3B, and 4.

In various embodiments, the acid gas stream 216 exiting the regenerator 212 contains a higher concentration of $H_2S$ than a typical solvent stream exiting a counter-current contactor. As a result, the sulfur recovery unit 218 of FIG. 2 may be more compact than a typical sulfur recovery unit that is used in conjunction with one or more counter-current contactors. Specifically, the sulfur recovery unit 218 may include smaller-diameter vessels than a typical sulfur recovery unit.

The simplified process flow diagram of FIG. 2 is not intended to indicate that the gas processing system 200 is to include all of the components shown in FIG. 2. Further, any number of additional components may be included within the gas processing system 200, depending on the details of the specific implementation. For example, the number of co-current contacting systems is not limited to that shown. Moreover, the interconnections do not have to be arranged as shown.

FIG. 3A is a process flow diagram of another gas processing system 300 that includes a co-current flow scheme and is configured for sulfur recovery using the LO-CAT® DirectTreat process. The gas processing system 300 is an alternative to the gas processing facility 100 discussed with respect to FIG. 1A. According to embodiments described herein, the gas processing system 300 is used for the removal of hydrogen sulfide ($H_2S$) and other acid gas components from a natural gas stream 302. The gas processing system 300 employs a number of co-current contacting systems 304A-F. Each co-current contacting system 304A-F includes a co-current contactor (not shown) and a separation system (not shown), as described further with respect to FIGS. 5, 6A, and 6B.

In various embodiments, the natural gas stream 302 is obtained from a hydrocarbon production operation. The natural gas stream 302 includes a non-absorbing hydrocarbon gas, such as methane, and one or more impurities, such as $H_2S$ and $CO_2$. In some embodiments, the natural gas stream 302 includes about 0.01% to about 10% $H_2S$ and about 1 to about 10% $CO_2$, along with the hydrocarbon gas. The gas processing system 300 converts the natural gas stream 302 into a sweetened natural gas stream 306 by removing the impurities from the natural gas stream 302.

In operation, the natural gas stream 302 is flowed into a first co-current contacting system 304A, where it is mixed with a solvent stream 308. The solvent stream 308 may be any treating liquid that is capable of removing $H_2S$ and other impurities from the natural gas stream 302. For example, in some embodiments, the solvent stream 308 includes FLEXSORB® SE or FLEXSORB® SE PLUS. However, in other embodiments, the solvent stream 308 may include monoethanolamine (MEA), 2(2-aminoethoxy) ethanol [Diglycolamine® (DGA)], diethanolamine (DEA), diisopropanolamine (DIM), methyldiethanolamine (MDEA), triethyleneamine, 2-amino-2-methyl-1-propanol (AMP), the UCARSOL™ family of products, or formulated MDEA solutions.

The solvent stream 308 may be a lean solvent stream that has undergone a desorption process for the removal of acid gas impurities. For example, in the gas processing system 300 shown in FIG. 3A, the solvent stream 308 introduced into the first co-current contacting system 304A includes a semi-lean solvent that is taken from a central portion of a regenerator 310. In addition, a lean solvent stream 312 taken from the regenerator 310 is directed into a final co-current contacting system 304F.

In various embodiments, the gas processing system 300 employs a series of co-current contacting systems 304A-F. Each co-current contacting system 304A-F removes a portion of the acid gas content from the natural gas stream 302, thereby releasing a progressively sweetened natural gas stream in a downstream direction. The final co-current contacting system 304F provides the final sweetened natural gas stream 306.

Before entering the first co-current contacting system 304A, the natural gas stream 302 passes through an inlet separator 314. The inlet separator 314 is used to clean the natural gas stream 302 by filtering out impurities, such as brine and drilling fluids. Some particle filtration may also take place. The cleaning of the natural gas stream 302 can prevent foaming of solvent during the acid gas treatment process.

In some embodiments, the natural gas stream 302 is also pretreated upstream of the inlet separator 314 or the first co-current contacting system 304A. For example, the natural gas stream 302 may undergo a water wash to remove glycol, methanol or other chemical additives. This may be accomplished via a separate processing loop (not shown) wherein water is introduced to the natural gas stream 302, such as via an additional co-current contacting system. Water has an affinity for glycol and will pull the glycol out of the natural gas stream 302. This, in turn, will help control foaming within the co-current contacting systems 304A-F.

As shown in FIG. 3A, the semi-lean solvent stream 308 is flowed into the first co-current contacting system 304A. Movement of the solvent stream 308 into the first co-current contacting system 304A is aided by pumps 316A and 316B and a cooler 318. The cooler 318 causes the solvent stream 308 to flow into the first co-current contacting system 304A at a suitable temperature, while the pumps 316A and 316B cause the solvent stream 308 to flow into the first co-current contacting system 304A at a suitable pressure of, for example, about 103 kPa (15 psig) to about 10.3 MPa (1,500 psig).

Once inside the first co-current contacting system 304A, the natural gas stream 302 and the solvent stream 308 move along the longitudinal axis of the first co-current contacting system 304A. As they travel, the liquid amine (or other treating solution) within the solvent stream 308 interacts with the $H_2S$ and other impurities within the natural gas stream 302, causing the $H_2S$ to chemically attach to or be absorbed by the amine molecules. A first partially-loaded, or "rich," solvent stream 320A is flowed out of the first co-current contacting system 304A. In addition, a first partially-sweetened natural gas stream 322A is flowed out of the first co-current contacting system 304A and into a second co-current contacting system 304B.

According to the embodiment shown in FIG. 3A, a third co-current contacting system 304C is provided after the second co-current contacting system 304B, and a fourth co-current contacting system 304D is provided after the third co-current contacting system 304C. In addition, a fifth co-current contacting system 304E is provided after the fourth co-current contacting system 304D, and a final co-current contacting system 304F is provided after the fifth co-current contacting system 304E. Each of the second, third, fourth, and fifth co-current contacting systems 304B, 304C, 304D, and 304E generates a respective partially-sweetened natural gas stream 322B, 322C, 322D, and 322E. In addition, each of the second, third, fourth, fifth, and final co-current contacting systems 304B, 304C, 304D, 304E, and 304F generates a respective partially-loaded solvent stream 320B, 320C, 320D, 320E, and 320F. In the gas processing system 300, the second partially-loaded solvent stream 320B merges with the first partially-loaded solvent stream 320A and goes through a regeneration process in the regenerator 310.

As the progressively-sweetened natural gas streams 322A-E are generated, the gas pressure in the gas processing system 300 will gradually decrease. As this occurs, the liquid pressures of the progressively-richer solvent streams 320A-F are correspondingly increased. This may be accomplished by placing one or more booster pumps (not shown) between each co-current contacting system 304A-F to boost liquid pressure in the gas processing system 300.

In the gas processing system 300, solvent streams are regenerated by flowing the partially-loaded solvent streams 320A and 320B through a flash drum 324. Absorbed natural gas 326 is flashed from the partially-loaded solvent streams 320A and 320B within the flash drum 324. The natural gas 326 is then flowed out of the flash drum 324 via an overhead line 328.

The resulting rich solvent stream 330 is flowed from the flash drum 324 to the regenerator 310. The rich solvent stream 330 is introduced into the regenerator 310 for desorption. The regenerator 310 includes a stripper portion 332 including trays or other internals (not shown). The stripper portion 332 is located directly above a reboiler portion 334. A heat source 336 is provided with the reboiler portion 334 to generate heat. The regenerator 310 produces the regenerated, lean solvent stream 312 that is recycled for re-use in the final co-current contacting system 304F. Stripped overhead gas from the regenerator 310, which includes concentrated $H_2S$ and $CO_2$, is flowed out of the regenerator 310 as an overhead impurities stream 338.

The overhead impurities stream 338 is flowed into a condenser 340, which cools the overhead impurities stream 338. The resulting cooled impurities stream 342 is flowed through a reflux accumulator 344. The reflux accumulator 344 separates any remaining liquid, such as condensed water, from the cooled impurities stream 342. This results in the generation of an acid gas stream 346 and a residual liquid stream 348.

The residual liquid stream 348 is flowed out of the bottom of the reflux accumulator 344. The residual liquid stream 348 is then flowed through a reflux pump 350, which boosts the pressure of the residual liquid stream 348 and pumps the residual liquid stream 348 into the regenerator 310. The residual liquid stream 348 is flowed out of the regenerator 310, for example, from the bottom of the reboiler portion 334 as part of the lean solvent stream 312. Some water may be added to the lean solvent stream 312 to balance the loss of water vapor to the partially sweetened natural gas streams 322A-E and acid gas stream 346. This water may be added at an intake or suction of the reflux pump 350.

The lean solvent stream 312 is at a low pressure. Accordingly, the lean solvent stream 312 is passed through a pressure boosting pump 352. From the pressure boosting pump 352, the lean solvent stream 312 is flowed through a cooler 354. The cooler 354 cools the lean solvent stream 312 to ensure that the lean solvent stream 312 will absorb acid gases effectively. The resulting lean solvent stream 356 is then used as the solvent stream for the final co-current contacting system 304F. Movement of the lean solvent stream 356 towards the final co-current contacting system 304F is aided by a pump 358. The pump 358 may cause the lean solvent stream 356 to flow at a suitable pressure, for example, of about 103 kPa (15 psig) to about 10.3 MPa (1,500 psig).

From the reflux accumulator 344, the acid gas stream 346 is flowed to a sulfur recovery unit 360. According to the embodiment shown in FIG. 3A, the sulfur recovery unit 360 employs the LO-CAT® DirectTreat process to convert the $H_2S$ within the acid gas stream 346 to elemental sulfur. Specifically, the acid gas stream 346 is flowed into an absorber 362 within the sulfur recovery unit 360. Within the absorber 362, the acid gas stream 346 reacts with a chelated iron solution 364 according to Eq. 2-4. In addition, hydrogen sulfide ($H_2S$) is removed from the carbon dioxide ($CO_2$) and other acid gas components within the acid gas stream 346, producing a treated gas 366 including primarily $CO_2$ and a concentrated solution 368 including the chelated iron solution 364 and sulfur.

The treated gas 366 is flowed out of the top of the absorber 362, while the concentrated solution 368 is flowed out of the bottom of the absorber 362 and into an oxidizer 370. Within the oxidizer 370, air from an air blower 372 moves uniformly through the concentrated solution 368. This results in the reduction of iron back to an active state according to Eq. 5 and 6, thus regenerating the chelated iron solution 364. In addition, chemical additions 374 are added to the chelated iron solution 364 within the oxidizer 370 to replace trace quantities of the chelated iron solution that are naturally lost through displacement, chelate degradation, and byproduct salt formation. The regenerated chelated iron solution 364 including the chemical additions 374 is then pumped back into the absorber 362 via a pump 376.

Vent gas 378 is flowed out of the top of the oxidizer 370 via an overhead line 380. The vent gas 378 may include residual nitrogen ($N_2$), oxygen ($O_2$), water ($H_2O$), carbon dioxide ($CO_2$), and trace hydrocarbons that were removed from the concentrated solution 368 within the oxidizer 370.

The sulfur within the concentrated solution 368 settles in the conical bottom section of the oxidizer 370, producing a sulfur slurry 382 that is then pumped into a sulfur filter 384. Within the sulfur filter 384, the sulfur slurry 382 is contacted with wash water 386, producing a sulfur cake 388 and a filtrate 390 including residual chelated iron solution. The filtrate 390 is then sent to a filtrate tank 392. From the filtrate tank 392, the filtrate 390 is pumped back into the oxidizer via a pump 394.

The process flow diagram of FIG. 3A is not intended to indicate that the gas processing system 300 is to include all of the components shown in FIG. 3A. Further, any number of additional components may be included within the gas processing system 300, depending on the details of the specific implementation. For example, the gas processing system 300 may include any suitable types of heaters, chillers, condensers, liquid pumps, gas compressors, blowers, bypass lines, other types of separation and/or fractionation equipment, valves, switches, controllers, and pressure-measuring devices, temperature-measuring devices, level-measuring devices, or flow-measuring devices, among others.

FIG. 3B is a process flow diagram of another gas processing system 396 that includes a co-current flow scheme and is configured for sulfur recovery using the LO-CAT® AutoCirc process. Like numbered items are as described with respect to FIG. 3A. The gas processing system 396 of FIG. 3B is the same as the gas processing system 300 of FIG. 3A, except that it includes a sulfur recovery unit 398 that employs the LO-CAT® AutoCirc process.

The equipment included within the sulfur recovery unit 398 of FIG. 3B is the same as the equipment included within the sulfur recovery unit 360 of FIG. 3A, except the sulfur recovery unit 398 of FIG. 3B does not include the absorber 362. According to the LO-CAT® AutoCirc process, the absorber 362 is omitted, and Eq. 2-6 are all performed within the oxidizer 370. This process is particularly suitable for acid gas streams that have been removed from a natural gas stream via an upstream gas purification process, such as the acid gas stream 346 of FIGS. 3A and 3B.

The process flow diagram of FIG. 3B is not intended to indicate that the gas processing system 396 is to include all of the components shown in FIG. 3B. Further, any number of additional components may be included within the gas processing system 396, depending on the details of the specific implementation.

Figure 4:
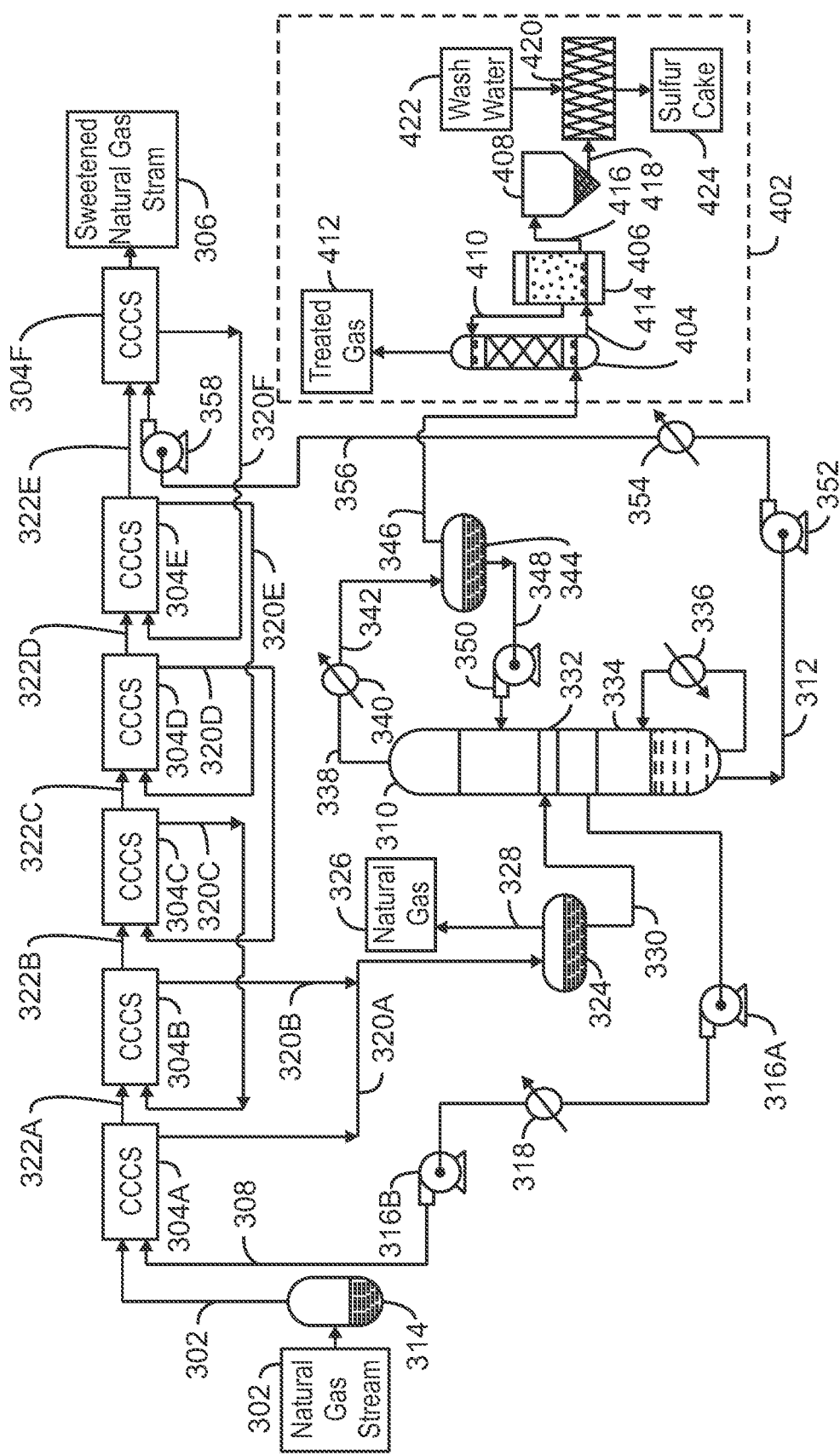
FIG. 4 is a process flow diagram of another gas processing system that includes a co-current flow scheme and is configured for sulfur recovery using the THIOPAQ O&G process.

FIG. 4 is a process flow diagram of another gas processing system 400 that includes a co-current flow scheme and is configured for sulfur recovery using the THIOPAQ O&G process. Like numbered items are as described with respect to FIGS. 3A and 3B. The gas processing system 400 of FIG. 4 is the same as the gas processing systems 300 and 396 of FIGS. 3A and 3B, except that it includes a sulfur recovery unit 402 that employs the THIOPAQ O&G process. More specifically, the sulfur recovery unit 402 employs the THIOPAQ O&G process to convert the H$_2$S within the acid gas stream 346 to elemental sulfur.

The THIOPAQ O&G process is a biological process for gas desulfurization and sulfur recovery that was developed by Pawn BV. The process is based on the sulfur oxidative properties of natural bacteria. As shown in FIG. 4, the THIOPAQ O&G process employs three main pieces of equipment, a contactor 404, a bioreactor 406, and a settler 408.

According to the embodiment shown in FIG. 4, the acid gas stream 346 is flowed into the bottom of the contactor 404. As the acid gas stream 346 moves upwards through the contactor 404, it makes contact with a downflowing aqueous bicarbonate solution 410, and the H$_2$S within the acid gas stream 346 is absorbed into the aqueous bicarbonate solution 410 as bisulfide ions, HS$^-$. This results in the production of a treated gas 412 including CO$_2$ (and other acid gas components) and a concentrated solution 414 including the aqueous bicarbonate solution 410 and the bisulfide ions.

The treated gas 412 is flowed out of the top of the contactor 404, while the concentrated solution 414 is flowed out of the bottom of the contactor 404 and into the bioreactor 406. Within the bioreactor 406, *Thiobacillus* bacteria within the aqueous bicarbonate solution 410 absorb the bisulfide ions, producing a sulfur-containing solution 416. The sulfur-containing solution 416 is then flowed into the top of the settler 408. The sulfur within the sulfur-containing solution 416 settles into the conical bottom section of the settler 408, producing a sulfur slurry 418 that is then pumped into a sulfur filter 420. Within the sulfur filter 420, the sulfur slurry 418 is contacted with wash water 422, producing a final sulfur cake 424 that is largely composed of elemental sulfur. Moreover, in some embodiments, a filtrate (not shown) exiting the sulfur filter 420 is pumped back into the settler 408.

The process flow diagram of FIG. 4 is not intended to indicate that the gas processing system 400 is to include all of the components shown in FIG. 4. Further, any number of additional components may be included within the gas processing system 400, depending on the details of the specific implementation. In various embodiments, using the THIOPAQ O&G process in conjunction with the co-current contacting systems 304A-F allows the THIOPAQ O&G sulfur recovery equipment to be much more compact than the sulfur recovery equipment that is typically used in conjunction with a conventional counter-current contactor. This may significantly reduce the operating expenses for the overall gas processing system 400.

According to the embodiments shown in FIGS. 3A, 3B, and 4, the co-current contacting systems 304A-F are connected in series. However, it is to be understood that the co-current contacting systems 304A-F may also be connected in parallel, or in any other suitable configuration. Moreover, while the embodiments shown in FIGS. 3A, 3B, and 4 include six co-current contacting systems 304A-F, it is to be understood that any number of co-current contacting systems may be included within the gas processing systems 300, 396, and 400, depending on the details of the specific implementation.

In some embodiments, the solvent stream 308 is a highly H$_2$S-selective solvent stream that is capable of selectively absorbing a higher concentration of H$_2$S as opposed to CO$_2$. For example, a tertiary amine (R$_1$R$_2$R$_3$—N) may be used. The reactions of acid gases with tertiary amines are shown below in Eq. 7 and 8.

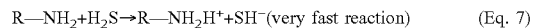

R—NH$_2$+H$_2$S→R—NH$_2$H$^+$+SH$^-$(very fast reaction) (Eq. 7)

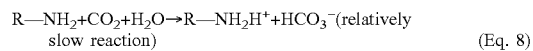

R—NH$_2$+CO$_2$+H$_2$O→R—NH$_2$H$^+$+HCO$_3^-$(relatively slow reaction) (Eq. 8)

As shown in Eq. 7, the reaction of H$_2$S with the tertiary amine is inherently very fast and is often considered instantaneous with respect to diffusion and other kinetic limitations. However, as shown in Eq. 8, the reaction of CO$_2$ with the tertiary amine is somewhat slower. The difference in these reaction rates can be utilized to selectively remove H$_2$S from the natural gas stream 302. Specifically, the contact time of the natural gas stream 302 and the solvent stream 308 can be minimized to enhance H$_2$S uptake over CO$_2$. This may be useful in shale gas applications, for example, where it is desirable to remove H$_2$S from the natural gas stream 302 without removing CO$_2$.

While the sulfur recovery units 360, 398, and 402 of FIGS. 3A, 3B, and 4 employ the LO-CAT® DirectTreat process, the LO-CAT® AutoCirc process, and the Thiopaq O&G process, respectively, it is to be understood that the gas processing system described herein may include any other suitable type of sulfur recovery unit. For example, the gas processing system described herein may include a sulfur recovery unit that utilizes the CrystaSulf® process developed by AECOM Process Technologies. More specifically, the CrystaSulf® process could be used to convert the H$_2$S within the acid gas stream 346 to elemental sulfur through a modified liquid-phase Claus reaction.

Furthermore, in some embodiments, a static mixer may be included within any of the sulfur recovery units 360, 398, and 402 described with respect to FIGS. 3A, 3B, and 4, respectively. Including a static mixer within the sulfur recovery units 360, 398, and 402 may further reduce the size of the equipment within the sulfur recovery units 360, 398, and 402, resulting in even higher cost savings. The static mixer may include internal baffles that provide a large amount of surface area for contacting the acid gas stream 346 with the process solution within the corresponding sulfur recovery unit 360, 398, or 402.

Co-Current Contacting System

Figure 5:
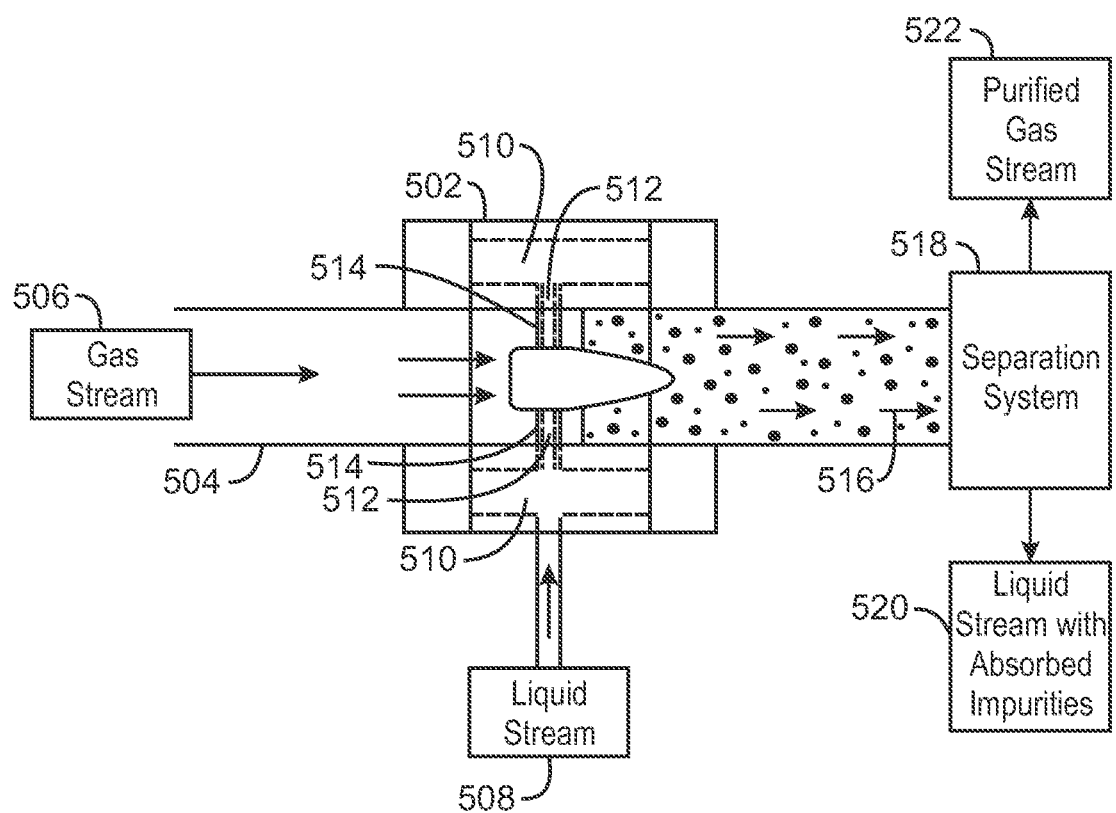
FIG. 5 is a schematic of a co-current contacting system.

FIG. 5 is a schematic of a co-current contacting system 500. The co-current contacting system 500 provides for the separation of components within a gas stream. In addition, the co-current contacting system 500 may aid in the implementation of various gas processing systems, such as the gas processing systems 200, 300, 396, and 400 of FIGS. 2, 3A, 3B, and 4, where the rapid separation of components is desired. In some embodiments, the co-current contacting system 500 is one of the co-current contacting systems 202A-C and 304A-F discussed with respect to FIGS. 2, 3A, 3B, and 4.

The co-current contacting system 500 includes a co-current contactor 502 that is positioned in-line within a pipe 504. The co-current contactor 502 includes a number of components that provide for the efficient contacting of a liquid droplet stream with a flowing gas stream 506. The liquid droplet stream is used for the separation of impurities, such as $H_2S$ and $CO_2$, from the gas stream 506.

As shown in FIG. 5, the gas stream 506 is flowed through the pipe 504 and into the co-current contactor 502. A liquid stream 508 is also flowed into the co-current contactor 502, for example, into a hollow space 510 coupled to flow channels 512 in the co-current contactor 502. The liquid stream 508 may include any type of treating liquid, or liquid solvent, that is capable of removing the impurities from the gas stream 506.

From the flow channels 512, the liquid stream 508 is released into the gas stream 506 as fine droplets through liquid injection orifices 514, resulting in a treated gas stream 516. The treated gas stream 516 includes small liquid droplets dispersed in a gas phase. The liquid droplets include impurities from the gas stream 506 that were absorbed or dissolved into the liquid stream 508.

The treated gas stream 516 is flowed into a separation system 518, such as a cyclonic separator, a mesh screen, or a settling vessel. The separation system 518 removes the liquid droplets from the gas phase. The liquid droplets include the original liquid stream with the absorbed impurities 520, and the gas phase includes a purified gas stream 522.

The schematic of FIG. 5 is not intended to indicate that the co-current contacting system 500 is to include all of the components shown in FIG. 5. Further, any number of additional components may be included within the co-current contacting system 500, depending on the details of the specific implementation.

Figure 6A:
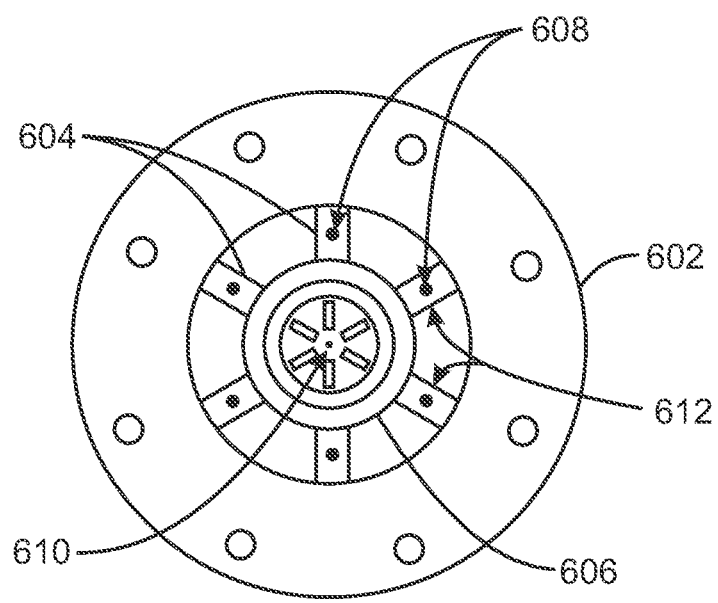
FIG. 6A is a front view of a co-current contactor.

FIG. 6A is a front view of a co-current contactor 600. In various embodiments, the co-current contactor 600 is implemented within a co-current contacting system, such as any of the co-current contacting systems 202A-C, 304A-F, and 500 described with respect to FIGS. 2, 3A, 3B, 4, and 5. The co-current contactor 600 is an axial, in-line co-current contactor located within a pipe (not shown). The front view of the co-current contactor 600 represents an upstream view of the co-current contactor 600.

The co-current contactor 600 includes an annular support ring 602, a number of radial blades 604 extending from the annular support ring 602, and a central gas entry cone 606. The annular support ring 602 secures the co-current contactor 600 in-line within the pipe. In addition, the radial blades 604 provide support for the central gas entry cone 606.

The annular support ring 602 may be designed as a flanged connection, or as a removable or fixed sleeve inside the pipe. In addition, the annular support ring 602 includes a liquid feed system and a hollow space described with respect to FIG. 5. A liquid stream is fed to the co-current contactor 600 via the hollow space in the annular support ring 602. The hollow space allows equal distribution of the liquid stream along the perimeter of the co-current contactor 600.

Small liquid channels within the annular support ring 602 provide a flow path for the liquid stream to flow through liquid injection orifices 608 within the radial blades 604. The liquid injection orifices 608 may be located on or near the leading edge of each radial blade 604. Placement of the liquid injection orifices 608 on the radial blades 604 allows the liquid stream to be uniformly distributed in a gas stream that is directed between the radial blades 604. Specifically, the liquid stream is contacted by the gas stream flowing through the gaps between the radial blades 604, and is sheared into small droplets and entrained in the gas phase.

The gas stream is also flowed into the central gas entry cone 606 through a gas inlet 610. The central gas entry cone 606 blocks a cross-sectional portion of the pipe. The radial blades 604 include gas exit slots 612 that allow the gas stream to be flowed out of the central gas entry cone 606. This increases the velocity of the gas stream as it flows through the pipe. The central gas entry cone 606 directs a predetermined amount of the gas stream to the gas exit slots 612 on the radial blades 604.

Some of the liquid stream injected through the radial blades 604 may be deposited on the surface of the radial blades 604 as a liquid film. As the gas stream flows through the central gas entry cone 606 and is directed out of the gas exit slots 612 on the radial blades 604, the gas stream may sweep, or blow, much of the liquid film off the radial blades 604. This may enhance the dispersion of the liquid stream into the gas phase. Further, the obstruction to the flow of the gas stream and the shear edges created by the central gas entry cone 606 may provide a zone with an increased turbulent dissipation rate. The may result in the generation of smaller droplets that enhance the mass transfer rate of the liquid stream and the gas stream.

The size of the co-current contactor 600 may be adjusted such that the gas stream flows at a high velocity. This may be accomplished by either a sudden reduction in the diameter of the annular support ring 602 or a gradual reduction in the diameter of the annular support ring 602. The outer wall of the co-current contactor 600 may be slightly converging in shape, terminating at the point where the gas stream and the liquid stream are discharged into the downstream pipe. This may allow for the shearing and re-entrainment of any liquid film that is removed from the co-current contactor 600. Further, a radial inward ring, grooved surface, or other suitable equipment may be included on the outer diameter of the co-current contactor 600 near the point where the gas stream and the liquid stream are discharged into the downstream pipe. This may enhance the degree of liquid entrainment within the gas phase.

The downstream end of the co-current contactor 600 may discharge into a section of pipe (not shown). The section of pipe may be a straight section of pipe, or a concentric expansion section of pipe. In some embodiments, the central gas entry cone 606 terminates with a blunt ended cone or a tapered ended cone. In other embodiments, the central gas entry cone 606 terminates with a ridged cone, which may include multiple concentric ridges along the cone that provide multiple locations for droplet generation. In addition, any number of gas exit slots may be provided on the cone itself to allow for the removal of the liquid film from the co-current contactor 600.

Figure 6B:
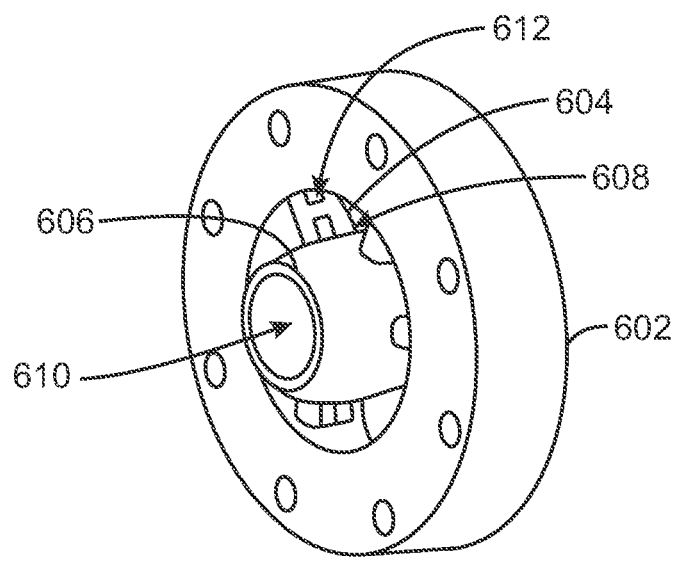
FIG. 6B is a side perspective view of the co-current contactor.

FIG. 6B is a side perspective view of the co-current contactor 600. Like numbered items are as described with respect to FIG. 6A. As shown in FIG. 6B, the upstream portion of the central gas entry cone 606 extends further into the pipe than the annular support ring 602 and the radial blades 604 in the upstream direction. The downstream portion of the central gas entry cone 606 may also extend further into the pipe than the annular support ring 602 and the radial blades 604 in the downstream direction. The length of the central gas entry cone 606 in the downstream direction depends on the type of cone at the end of the central gas entry cone 606. Terminating the central gas entry cone 606 with a tapered ended cone (not shown) may reduce the overall pressure drop in the pipe caused by the co-current contactor 600. On the other hand, terminating the central gas entry cone 606 with a blunt ended cone (not shown) may encourage droplet formation in the center of the pipe.

Method for Sulfur Recovery within a Gas Processing System

Figure 7:
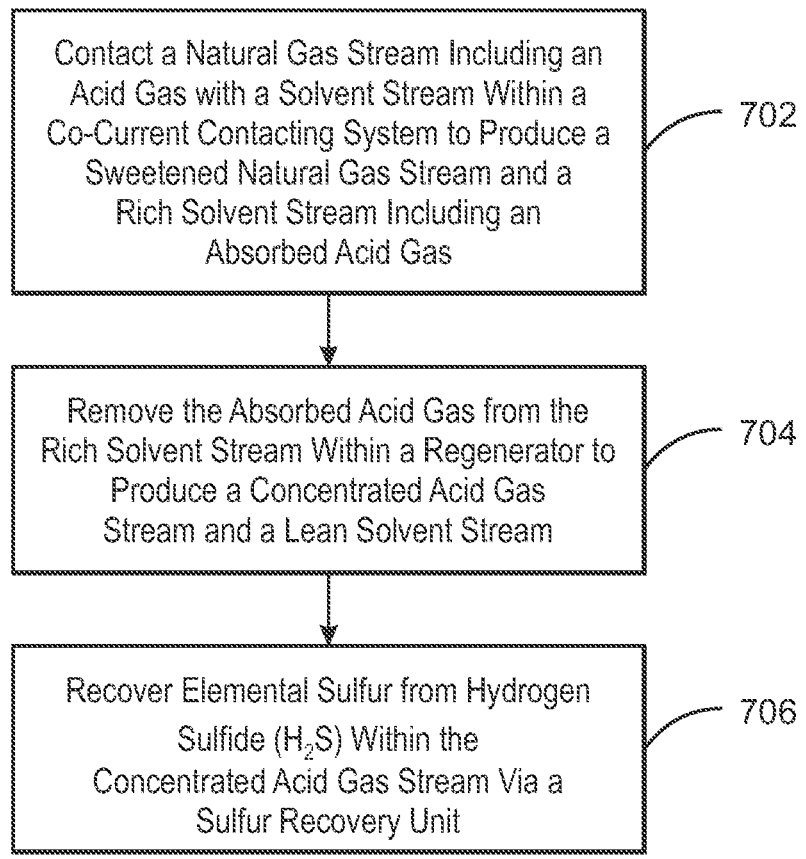
FIG. 7 is a process flow diagram showing a method for sulfur recovery within a gas processing system.

FIG. 7 is a process flow diagram showing a method 700 for sulfur recovery within a gas processing system. The method 700 is implemented by a gas processing system, such as the gas processing systems 200, 300, 396, and 400 discussed with respect to FIGS. 2, 3A, 3B, and 4.

The method begins at block 702, at which a natural gas stream including an acid gas is contacted with a solvent stream within a co-current contacting system to produce a sweetened natural gas stream and a rich solvent stream including absorbed acid gas. In various embodiments, the acid gas within the natural gas stream includes $H_2S$ and $CO_2$, and the solvent stream is an $H_2S$-selective solvent stream. Moreover, the co-current contacting system may be any of the co-current contacting systems 202A-C, 304A-F, and 500 described with respect to FIGS. 2, 3A, 3B, 4, and 5.

According to embodiments described herein, contacting the natural gas stream with the solvent stream within the co-current contacting system includes flowing the solvent stream into a co-current contactor via an annular support ring and a number of radial blades extending from the annular support ring, wherein the annular support ring secures the co-current contactor in-line within a pipe. Contacting the natural gas stream with the solvent stream within the co-current contacting system also includes flowing the natural gas stream into the co-current contactor via a central gas entry cone that is supported by the number of radial blades, wherein a first portion of the natural gas stream flows through the central gas entry cone and a second portion of the natural gas stream flows around the central gas entry cone between the number of radial blades. Contacting the natural gas stream with the solvent stream within the co-current contacting system further includes contacting the natural gas stream with the solvent stream to provide for incorporation of liquid droplets formed from the solvent stream into the natural gas stream such that the acid gas from the natural gas stream is absorbed by the liquid droplets, and separating the liquid droplets including the absorbed acid gas from the natural gas stream within a separator, producing the sweetened natural gas stream and the rich solvent stream.

At block 704, the absorbed acid gas is removed from the rich solvent stream within a regenerator to produce a concentrated acid gas stream and a lean solvent stream. In some embodiments, the lean solvent stream is then sent back into the co-current contacting system as the solvent stream.

At block 706, elemental sulfur is recovered from the $H_2S$ within the concentrated acid gas stream via a sulfur recovery unit. The sulfur recovery unit may employ any suitable sulfur recovery process to recover the elemental sulfur from the $H_2S$. For example, the sulfur recovery unit may employ the LO-CAT® DirectTreat process, the LO-CAT® AutoCirc process, the Thiopaq O&G process, or the Crystasulf® process, depending on the details of the specific implementation. Moreover, the sulfur recovery unit may also include a static mixer to increase the efficiency of the system.

The process flow diagram of FIG. 7 is not intended to indicate that the steps of the method 700 are to be executed in any particular order, or that all of the steps of the method 700 are to be included in every case. Further, any number of additional steps not shown in FIG. 7 may be included within the method 700, depending on the details of the specific implementation.

While the present techniques may be susceptible to various modifications and alternative forms, the embodiments discussed above have been shown only by way of example. However, it should again be understood that the techniques are not intended to be limited to the particular embodiments disclosed herein. Indeed, the present techniques include all alternatives, modifications, and equivalents falling within the true spirit and scope of the appended claims.

What is claimed is:

1. A gas processing system, comprising:
   a co-current contacting system configured to:
      contact a natural gas stream comprising an acid gas with a solvent stream to produce a sweetened natural gas stream and a rich solvent stream comprising an absorbed acid gas; and
      send the rich solvent stream to a regenerator;
   the regenerator configured to:
      remove the absorbed acid gas from the rich solvent stream to produce a concentrated acid gas stream and a lean solvent stream; and
      send the concentrated acid gas stream to a sulfur recovery unit; and
   the sulfur recovery unit configured to recover elemental sulfur from hydrogen sulfide (H2S) within the concentrated acid gas stream; and
   the co-current contacting system further comprising:
      a co-current contactor located in-line within a pipe, the co-current contactor comprising:
         an annular support ring configured to maintain the co-current contactor within the pipe;
         a plurality of radial blades configured to allow the solvent stream to flow into the co-current contactor; and
         a central gas entry cone configured to allow the natural gas stream to flow through a hollow section within the co-current contactor;
         wherein the co-current contactor provides for efficient incorporation of liquid droplets formed from the solvent stream into the natural gas stream such that the acid gas from the natural gas stream is absorbed by the liquid droplets; and
      a separation system configured to remove the liquid droplets comprising the absorbed acid gas from the natural gas stream, producing the sweetened natural gas stream and the rich solvent stream.

2. The gas processing system of claim 1, wherein the sulfur recovery unit comprises:
   an absorber configured to contact the concentrated acid gas stream with a chelated iron solution to produce a treated gas stream and a concentrated solution comprising the chelated iron solution and sulfur;
   an oxidizer configured to separate the concentrated solution into a sulfur slurry, a vent gas stream, and a regenerated chelated iron solution; and
   a sulfur filter configured to produce a sulfur cake from the sulfur slurry.

3. The gas processing system of claim 1, wherein the sulfur recovery unit comprises:
   an oxidizer configured to contact the concentrated acid gas stream with a chelated iron solution to produce a sulfur slurry; and
   a sulfur filter configured to produce a sulfur cake from the sulfur slurry.

4. The gas processing system of claim 1, wherein the sulfur recovery unit comprises:
a contactor configured to contact the concentrated acid gas stream with an aqueous bicarbonate solution such that the H2S within the concentrated acid gas stream is absorbed into the aqueous bicarbonate solution as bisulfide ions;
a bioreactor configured to contact the aqueous bicarbonate solution comprising the bisulfide ions with *Thiobacillus* bacteria to produce a sulfur-containing solution;
a settler configured to produce a sulfur slurry from the sulfur-containing solution; and
a sulfur filter configured to produce a sulfur cake from the sulfur slurry.

5. The gas processing system of claim 1, wherein the sulfur recovery unit utilizes a modified liquid-phase Claus reaction.

6. The gas processing system of claim 1, wherein the solvent stream comprises an H2S-selective solvent stream.

7. The gas processing system of claim 1, wherein the gas processing system is configured to send the lean solvent stream from the regenerator back into the co-current contacting system as the solvent stream.

8. The gas processing system of claim 1, comprising a plurality of co-current contacting systems configured to produce a progressively sweetened natural gas stream and a progressively richer solvent stream comprising an increasing concentration of the absorbed acid gas, wherein at least one of the plurality of co-current contacting systems is configured to send a corresponding progressively richer solvent stream to the regenerator.

9. The gas processing system of claim 8, wherein each of the plurality of co-current contacting systems is configured to recirculate a corresponding progressively richer solvent stream to a preceding one of the plurality of co-current contacting systems.

10. A method for recovering sulfur within a gas processing system, comprising:
contacting a natural gas stream comprising an acid gas with a solvent stream within a co-current contacting system to produce a sweetened natural gas stream and a rich solvent stream comprising an absorbed acid gas;
removing the absorbed acid gas from the rich solvent stream within a regenerator to produce a concentrated acid gas stream and a lean solvent stream; and
recovering elemental sulfur from hydrogen sulfide (H2S) within the concentrated acid gas stream via a sulfur recovery unit;
wherein contacting the natural gas stream comprising the acid gas with the solvent stream within the co-current contacting system comprises:
flowing the solvent stream into a co-current contactor via an annular support ring and a plurality of radial blades extending from the annular support ring, wherein the annular support ring secures the co-current contactor in-line within a pipe;
flowing the natural gas stream into the co-current contactor via a central gas entry cone that is supported by the plurality of radial blades, wherein a first portion of the natural gas stream flows through the central gas entry cone and a second portion of the natural gas stream flows around the central gas entry cone between the plurality of radial blades;
contacting the natural gas stream with the solvent stream to provide for incorporation of liquid droplets formed from the solvent stream into the natural gas stream such that the acid gas from the natural gas stream is absorbed by the liquid droplets; and
separating the liquid droplets comprising the absorbed acid gas from the natural gas stream within a separator, producing the sweetened natural gas stream and the rich solvent stream.

11. The method of claim 10, wherein recovering the elemental sulfur from the H2S within the concentrated acid gas stream via the sulfur recovery unit comprises:
contacting the concentrated acid gas stream with a chelated iron solution within an absorber to produce a treated gas stream and a concentrated solution comprising the chelated iron solution and sulfur;
separating the concentrated solution into a sulfur slurry, a vent gas stream, and a regenerated chelated iron solution within an oxidizer; and
producing a sulfur cake from the sulfur slurry using a sulfur filter.

12. The method of claim 10, wherein recovering the elemental sulfur from the H2S within the concentrated acid gas stream via the sulfur recovery unit comprises:
contacting the concentrated acid gas stream with a chelated iron solution within an oxidizer to produce a sulfur slurry; and
producing a sulfur cake from the sulfur slurry using a sulfur filter.

13. The method of claim 10, wherein recovering the elemental sulfur from the H2S within the concentrated acid gas stream via the sulfur recovery unit comprises:
contacting the concentrated acid gas stream with an aqueous bicarbonate solution within a contactor such that the H2S within the concentrated acid gas stream is absorbed into the aqueous bicarbonate solution as bisulfide ions;
contacting the aqueous bicarbonate solution comprising the bisulfide ions with *Thiobacillus* bacteria within a bioreactor to produce a sulfur-containing solution;
producing a sulfur slurry from the sulfur-containing solution within a settler; and
producing a sulfur cake from the sulfur slurry using a sulfur filter.

14. The method of claim 10, wherein recovering the elemental sulfur from the H2S within the concentrated acid gas stream via the sulfur recovery unit comprises using a modified liquid-phase Claus reaction to recover the elemental sulfur from the H2S.

15. The method of claim 10, wherein the solvent stream comprises an H2S-selective solvent stream.

16. The method of claim 10, comprising sending the lean solvent stream from the regenerator back into the co-current contacting system as the solvent stream.

17. A gas processing system, comprising:
a first co-current contacting system configured to:
contact a natural gas stream comprising an acid gas with a first solvent stream to produce a first partially-sweetened natural gas stream and a first rich solvent stream comprising a first portion of absorbed acid gas; and
send the first rich solvent stream to a regenerator; and
wherein the first co-current contacting system comprises:
a co-current contactor located in-line within a pipe, the co-current contactor comprising:
an annular support ring configured to maintain the co-current contactor within the pipe;

a plurality of radial blades configured to allow the first solvent stream to flow into the co-current contactor; and a central gas entry cone configured to allow the natural gas stream to flow through a hollow section within the co-current contactor;

wherein the co-current contactor provides for efficient incorporation of liquid droplets formed from the first solvent stream into the natural gas stream such that the acid gas from the natural gas stream is absorbed by the liquid droplets; and a separation system configured to remove the liquid droplets comprising the absorbed acid gas from the natural gas stream, producing the first partially-sweetened natural gas stream and the first rich solvent stream;

a second co-current contacting system configured to:

contact the first partially-sweetened natural gas stream with a second solvent stream to produce a second partially-sweetened natural gas stream and a second rich solvent stream comprising a second portion of absorbed acid gas; and send the second rich solvent stream back into the first co-current contacting system as the first solvent stream;

a third co-current contacting system configured to:

contact the second partially-sweetened natural gas stream with a third solvent stream to produce a sweetened natural gas stream and a third rich solvent stream comprising a third portion of absorbed acid gas; and send the third rich solvent stream back into the second co-current contacting system as the second solvent stream;

the regenerator configured to:

remove the first portion of the absorbed acid gas from the first solvent stream to produce a concentrated acid gas stream and a lean solvent stream;

send the lean solvent stream into the third co-current contacting system as the third solvent stream; and send the concentrated acid gas stream to a sulfur recovery unit; and the sulfur recovery unit configured to recover elemental sulfur from hydrogen sulfide (H2S) within the concentrated acid gas stream.

18. The gas processing system of claim 17, wherein the sulfur recovery unit comprises:

an absorber configured to contact the concentrated acid gas stream with a chelated iron solution to produce a treated gas stream and a concentrated solution comprising the chelated iron solution and sulfur;

an oxidizer configured to separate the concentrated solution into a sulfur slurry, a vent gas stream, and a regenerated chelated iron solution; and a sulfur filter configured to produce a sulfur cake from the sulfur slurry.

* * * * *